(12) United States Patent
Pedlick et al.

(10) Patent No.: US 6,270,518 B1
(45) Date of Patent: Aug. 7, 2001

(54) WEDGE SHAPED SUTURE ANCHOR AND METHOD OF IMPLANTATION

(75) Inventors: Jack S. Pedlick, Butler; Thu Anh Le, Matawan; John DiGiovanni, Woodbridge; Dennis D. Jamiolkowski, Long Valley; Mark J. Suseck, Flemington, all of NJ (US)

(73) Assignee: Mitek Surgical Products, Inc., Westwood, MA (US)

( * ) Notice: Subject to any disclaimer, the term of this patent is extended or adjusted under 35 U.S.C. 154(b) by 0 days.

(21) Appl. No.: 09/412,903

(22) Filed: Oct. 5, 1999

Related U.S. Application Data

(63) Continuation of application No. 08/630,389, filed on Apr. 10, 1996, now Pat. No. 5,961,538.

(51) Int. Cl.[7] ........................................ A61B 17/04
(52) U.S. Cl. .......................... 606/232; 606/72; 606/132
(58) Field of Search .................................... 606/232, 104, 606/132, 139, 72, 73

(56) References Cited

U.S. PATENT DOCUMENTS

| | | |
|---|---|---|
| 1,538,173 | 5/1925 | Daughaday . |
| 3,254,890 | 6/1966 | Watson ................................. 273/33 |
| 3,907,289 | 9/1975 | Bondu, Sr. ............................ 273/33 |

(List continued on next page.)

FOREIGN PATENT DOCUMENTS

| | | |
|---|---|---|
| 2045903 | 1/1992 | (CA) . |
| 2046010 | 1/1992 | (CA) . |
| WO 9309730 | 5/1993 | (WO) . |

OTHER PUBLICATIONS

Richmond et al., "Modification of the Bankart Reconstruction with a Suture Anchor", The American Journal of Sports Medicine, vol. 19, No. 4, pp. 343–346 (Jul./Aug. 1991).

(List continued on next page.)

*Primary Examiner*—Gary Jackson
(74) *Attorney, Agent, or Firm*—Pandiscio & Pandiscio

(57) ABSTRACT

A suture anchor is described which in one form may be easily fabricated from extruded material by angular cuts and bore holes which provide an offset pulling force to the suture. In an alternate and preferred embodiment the suture anchor is injection molded having an annular displaced corner and abutment wall which act to seat the suture anchor firmly within a bore hole. Novel application means are also disclosed which hold the suture anchor on a frangible shaft for insertion and upon completion of the insertion permit fracture of the frangible portion and removal of the instrument. In another form of the invention, the suture anchor comprises a substantially wedge-shaped body having a smaller distal end and a larger proximal end, means thereon for retaining a suture, and means thereon for releasable connection to an inserter shaft; a boundary surface and a plow surface of the body intersecting to form a biting edge at the proximal end of the body; and the boundary surface and an abutment surface of the body intersecting to form a cam surface at the proximal end of the body; and the biting edge being adapted to be in engagement with a first wall portion of a bore in a bone and the cam surface being adapted to be in engagement with a second wall portion of the bore opposed to the first wall portion; wherein tension on the inserter shaft is operable to move the cam portion along the bore second wall portion and rotate the body in the bore such that the biting edge bites into the bore first wall portion to lock the body in the bore.

1 Claim, 40 Drawing Sheets

U.S. PATENT DOCUMENTS

| | | |
|---|---|---|
| 3,973,277 | 8/1976 | Semple et al. .................. 3/1 |
| 4,386,971 | 6/1983 | Melton et al. .................. 148/11.5 R |
| 4,404,025 | 9/1983 | Mercier et al. .................. 148/11.5 F |
| 4,502,896 | 3/1985 | Duerig et al. .................. 148/11.5 F |
| 4,505,767 | 3/1985 | Quin .................. 148/402 |
| 4,524,765 | 6/1985 | de Zbikowski .................. 128/92 D |
| 4,533,411 | 8/1985 | Melton .................. 148/402 |
| 4,553,543 | 11/1985 | Amarasinghe .................. 128/334 R |
| 4,565,589 | 1/1986 | Harrison .................. 148/402 |
| 4,605,414 | 8/1986 | Czajka .................. 623/13 |
| 4,632,100 | 12/1986 | Somers et al. .................. 128/92 |
| 4,669,473 | 6/1987 | Richards et al. .................. 128/334 |
| 4,669,725 | 6/1987 | Taylor .................. 273/33 |
| 4,678,470 | 7/1987 | Nashef et al. .................. 623/16 |
| 4,738,255 | 4/1988 | Goble et al. . |
| 4,741,330 | 5/1988 | Hayhurst . |
| 4,832,026 | 5/1989 | Jones . |
| 4,898,156 | 2/1990 | Gatturna et al. .................. 606/72 |
| 4,899,743 | 2/1990 | Nicholson et al. .................. 606/139 |
| 4,932,973 | 6/1990 | Gendler .................. 623/16 |
| 4,946,468 | 8/1990 | Li .................. 606/232 |
| 4,950,296 | 8/1990 | McIntyre .................. 623/16 |
| 4,968,315 | 11/1990 | Gatturna .................. 606/72 |
| 4,968,316 | 11/1990 | Hergenroeder .................. 606/90 |
| 5,002,550 | 3/1991 | Li .................. 606/139 |
| 5,011,473 | 4/1991 | Gatturna .................. 604/51 |
| 5,041,129 | 8/1991 | Hayhurst et al. .................. 606/232 |
| 5,046,513 | 9/1991 | Gatturna et al. .................. 128/898 |
| 5,067,962 | 11/1991 | Campbell et al. .................. 623/13 |
| 5,073,373 | 12/1991 | O'Leary et al. .................. 424/422 |
| 5,100,417 | 3/1992 | Cerier et al. .................. 606/139 |
| 5,102,421 | 4/1992 | Anspach, Jr. .................. 606/232 |
| 5,112,354 | 5/1992 | Sires .................. 623/16 |
| 5,141,520 | 8/1992 | Goble et al. .................. 606/232 |
| 5,156,616 | 10/1992 | Meadows et al. .................. 606/232 |
| 5,174,087 | 12/1992 | Bruno .................. 53/430 |
| 5,176,682 | 1/1993 | Chow .................. 606/72 |
| 5,179,915 | 1/1993 | Cohen et al. .................. 606/62 |
| 5,192,303 | 3/1993 | Gatturna et al. .................. 606/232 |
| 5,203,787 | 4/1993 | Noblitt et al. .................. 606/232 |
| 5,207,679 | 5/1993 | Li .................. 606/72 |
| 5,211,647 | 5/1993 | Schmieding .................. 606/104 |
| 5,217,486 | 6/1993 | Rice et al. .................. 606/232 |
| 5,258,016 | 11/1993 | DiPoto et al. .................. 606/232 |
| 5,269,809 | 12/1993 | Hayhurst et al. .................. 606/232 |
| 5,290,558 | 3/1994 | O'Leary et al. .................. 424/422 |
| 5,298,254 | 3/1994 | Prewett et al. .................. 424/422 |
| 5,312,438 | 5/1994 | Johnson .................. 606/232 |
| 5,423,860 | 6/1995 | Lizardi et al. .................. 606/232 |
| 5,439,684 | 8/1995 | Prewett et al. .................. 424/422 |
| 5,464,425 | 11/1995 | Skiba .................. 606/232 |
| 5,492,697 | 2/1996 | Boyan et al. .................. 424/422 |
| 5,540,718 * | 7/1996 | Bartlett .................. 606/232 |
| 5,683,418 * | 11/1997 | Luscombe et al. .................. 606/104 |

OTHER PUBLICATIONS

Wolf, "Arthroscopic Capsulolabral Repair Using Suture Anchors", Orthopedic Clinics of North America, vol. 24, No. 1, pp. 59–69 (Jan. 1993).

Carpenter et al., "Pull–Out Strength of Five Suture Anchors", The Journal of Arthroscopic and Related Surgery, vol. 9, No. 1, pp. 109–113 (Feb. 1993).

* cited by examiner

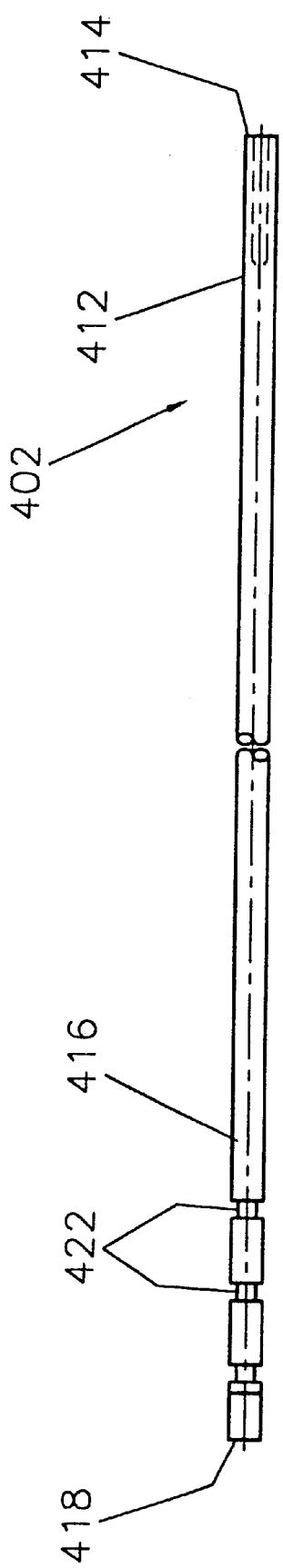
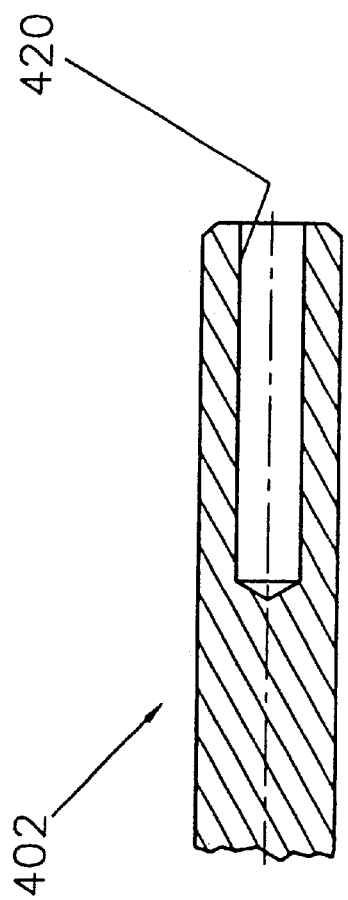
FIG. 44
FIG. 45

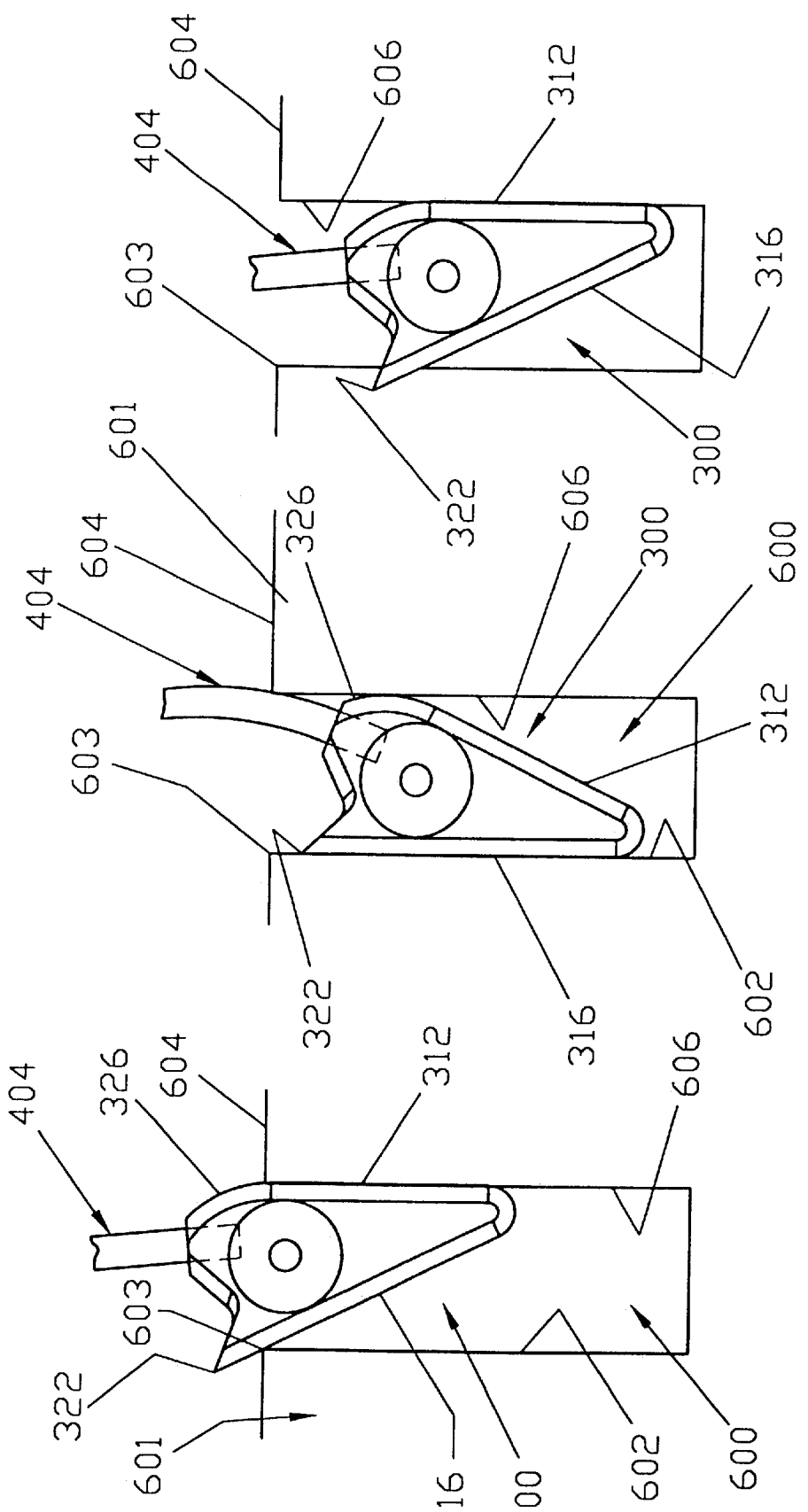

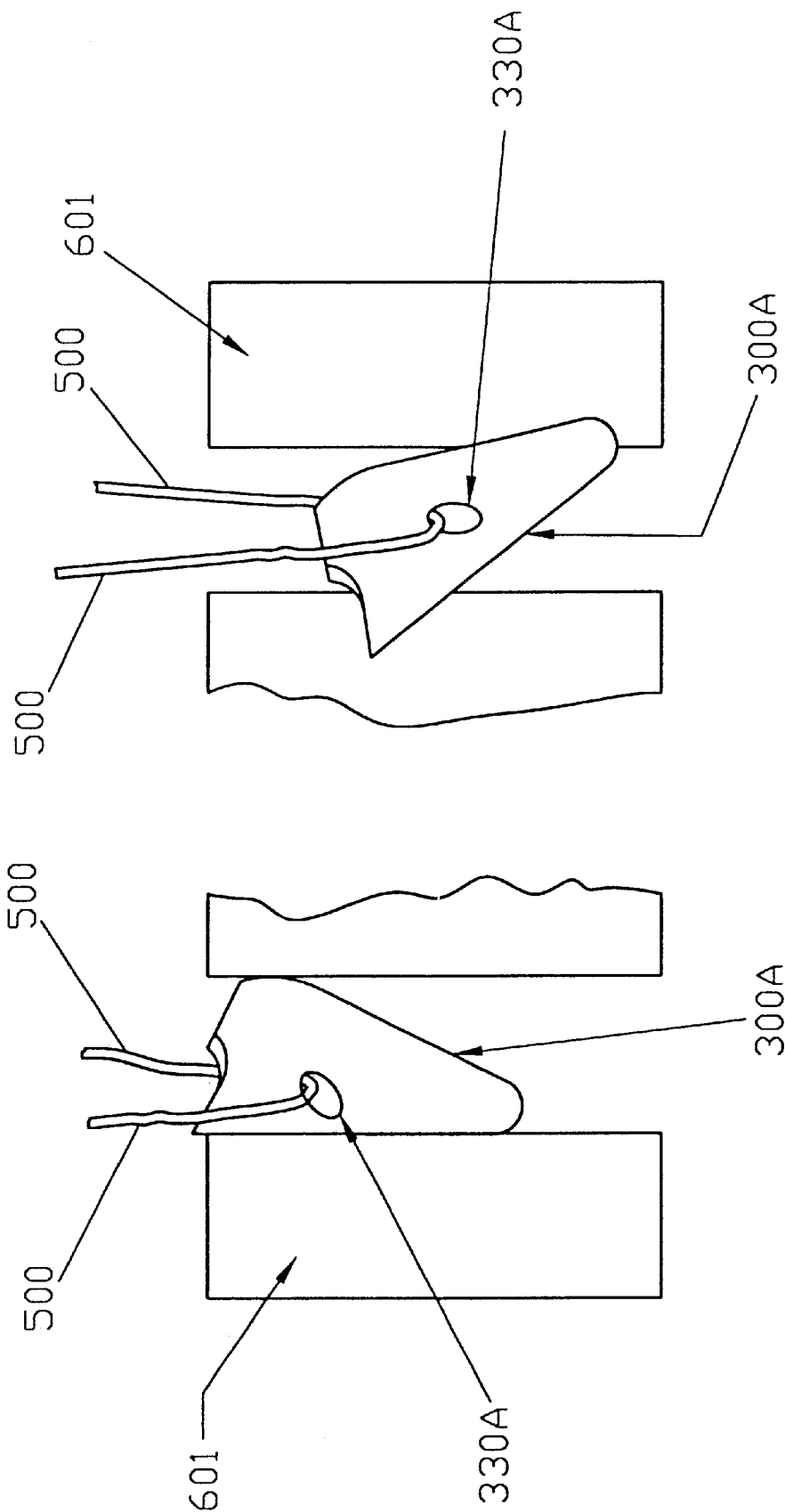

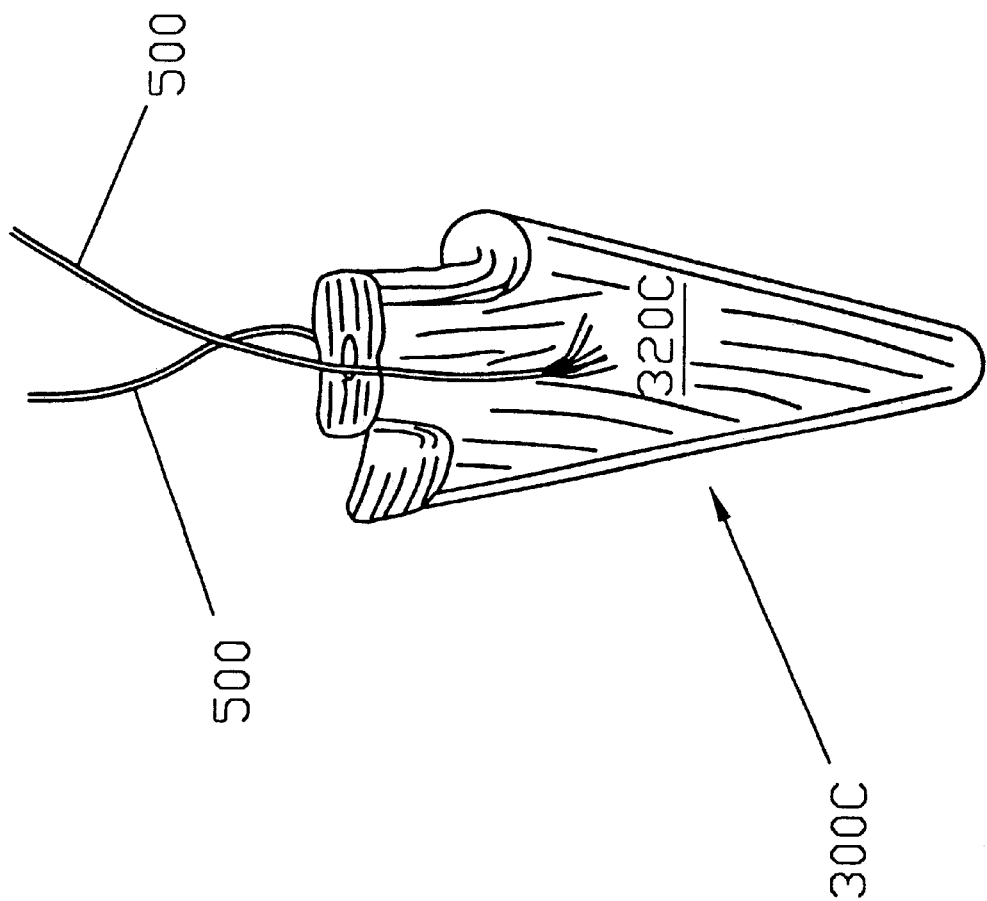

WEDGE SHAPED SUTURE ANCHOR AND METHOD OF IMPLANTATION

This is a continuation of U.S. patent application Ser. No. 08/630,389, filed Apr. 10, 1996 now U.S. Pat. No. 5,961,538.

TECHNICAL FIELD

The field of art to which this invention relates is surgical implements and more specifically suture anchors for anchoring suture material to bone.

BACKGROUND ART

As the treatment of injuries to joints and soft tissue has progressed in the orthopaedic medical arts, there has been a need for medical devices which can be used to attach tendons, ligaments and other soft tissue to bone. When surgically repairing an injured joint, for example, it is often preferable to restore the joint by reattaching the damaged soft tissues rather than replacing them with an artificial material. Such restorations typically require the attachment of soft tissue such as ligaments and tendons to bone.

An increase in the incidence of injuries to joints involving soft tissue has been observed. This increased incidence may be due, at least in part, to an increase in participation by the public in various physical activities such as sports and other recreational activities. These types of activities may increase the loads and stress placed upon joints, sometimes resulting in joint injuries with corresponding damage to associated soft tissue. In 1991, for example, there were approximately 560,000 surgical procedures performed in the United States in which soft tissue was attached to a bone in various joints including the shoulder, hip and knee.

One conventional orthopaedic procedure for reattaching soft tissue to bone is performed by initially drilling holes or tunnels at predetermined locations through a bone in the vicinity of a joint. Then, the surgeon approximates soft tissue to the surface of the bone using sutures threaded through these holes or tunnels. This method, although effective, is a time consuming procedure resulting in the generation of numerous bone tunnels. A known complication of drilling tunnels across bone is that nerves and other soft tissue structures may be injured by the drill bit or orthopaedic pin as it exits the far side of the bone. Also, it is anatomically very difficult to reach and/or secure a suture/wire that has been passed through a tunnel. When securing the suture or wire on the far side of the bone, nerves and soft tissues can become entrapped and damaged.

In order to overcome some of the problems associated with the use of the conventional bone tunnel procedures, suture anchors have been developed and are frequently used to attach soft tissue to bone. A suture anchor is an orthopaedic, medical device which is typically implanted into a cavity drilled into a bone. Although less frequently, these devices have also been referred to as bone anchors. The cavity is typically referred to as a bore hole and usually does not extend through the bone. This type of bore hole is typically referred to as a "ublind hole". The bore hole is typically drilled through the outer cortex layer of the bone and into the inner cancellous layer. The suture anchor may be engaged in the bore hole by a variety of mechanisms including friction fit, barbs which are forced into the cancellous layer of bone, etc. Suture anchors are known to have many advantages including reduced bone trauma, simplified application procedures, and decreased likelihood of suture failure due to abrasion on bone. Suture anchors may be used in the Bankart shoulder reconstruction for repairing the glenohumeral ligament and may also be used in surgical procedures such as rotator cuff repair and hip replacement. Also, such anchors may be used in repair of tendon tears by direct attachment of bone to bone.

Suture anchors typically have at least one suture attached. This may be by means of a hole or opening for receiving the suture(s). At least one end and typically both ends of the suture strand extend out from the bore hole and are used to attach soft tissue. The suture anchors presently described in the art may be made of absorbable materials which absorb over time, or they may be made from various non-absorbable, biocompatible materials. Although most suture anchors described in the art are made from non-absorbable materials, the use of absorbable suture anchors may result in fewer complications since the suture anchor is absorbed and replaced by bone over time. In addition, the use of absorbable suture anchors may reduce the likelihood of damage to local joints caused by anchor migration.

Although suture anchors for attaching soft tissue to bone are available for use by the orthopaedic surgeon, there is a constant need in this art for novel suture anchors having improved performance characteristics.

SUMMARY OF THE INVENTION

The device of the present invention calls for an implantable apparatus for wedging within an opening formed within a bone. The apparatus comprises a body which defines a perimeter and said perimeter defining at least one biting edge. A hole is defined by the body through which a suture is received for attachment through the device to the bone. The hole defined by the body may be nearer to one side of the perimeter in order to provide an imbalance of force to increase rotation of the device during the implantation procedure. The body in cross-section may have a perimeter which is substantially in the shape of a triangle, trapezoid or parallelogram. In this way the body may have two sides which diverge in a direction away from said hole, such that the rotation causes an edge formed by one of such sides to bite into the soft cancellous layer of the bone. In order to better distribute the forces acting on the device, the sides may be rounded so that the rounded edge will match with the size of the bore hold provided in the bone. In this way, maximum contact of the edge with the side of the hole in the bone is provided.

The edge may be formed by the intersection of planar or rounded sides or a combination of planar and rounded sides in order to optimize the biting action of the edge. The edge may also be provided with a single engaging tooth or a plurality of engaging teeth in order to improve the holding power, biting and/or placement of the device. The device may be triangular in shape and thus formed by three mutually adjacent sides.

The apparatus may further include a thin longitudinal stem portion which extends from the body. This stem portion is preferably detachable from the body and may be integral and formed with the body out of the same material and provided with a frangible portion or may be formed separately and fitted to the body.

The body may be made of any medical grade material and the stem may be made of a different medical grade material. The body and stem may be joined by a frangible portion which could be formed, for example, by two intersecting web portions in order to provide stability to the device during insertion while still providing the weakness necessary for fracture of the area.

The stem may be provided with a protrusion which mates with an implantation device in order to position the stem within the implantation device at an optimum position.

The body may be made of bioabsorbable material, a biocompatible metal, or a medical grade polymer for example. The body may be of a medical grade metal material and the stem made of a bioabsorbable polymer such that after fraction the anchor stays implanted but the stem portion remaining after fracture is absorbed by the body.

The invention includes a method of implanting a device for holding material in the bone which comprises accessing the bone and forming an opening therein for receipt of the device. The device is then gripped by a stem which extends from the device and is inserted into the opening by gripping such a stem. The stem is then detached from the device and the device is rotated in order to wedge within the opening formed in the bone.

The separation of the stem from the device may include either breaking a portion of the stem or device in order to separate the stem and device or separating the stem via a snap fit, interference fit, or other attachment mechanism.

The insertion device may include a stabilizing portion to prevent excessive premature rotation of the device and thus prevent premature fracture of any frangible portion of the stem. This however is not necessary in the method where the device is attached to the stem through an interference or frictional fit and the stem is merely removed from an opening in the device during the method of implantation.

In another form of the invention, the suture anchor can comprise a substantially wedge-shaped body having a smaller distal end and a larger proximal end, means thereon for retaining a suture, and means thereon for releasable connection to an inserter shaft; a boundary surface and a plow surface of the body intersecting to form a biting edge at the proximal end of the body; and the boundary surface and an abutment surface of the body intersecting to form a cam surface at the proximal end of the body; and the biting edge being adapted to be in engagement with a first wall portion of the bore and the cam surface being adapted to be in engagement with a second wall portion of the bore opposed to the first wall portion; wherein tension on the inserter shaft is operable to move the cam portion along the bore second wall portion and rotate the body in the bore such that the biting edge bites into the bore first wall portion to lock the body in the bore.

And in another form of the invention, the suture anchor can comprise a substantially wedge-shaped body having a smaller distal end and a larger proximal end, the body defining a hole therethrough for retaining a suture, and the body having means thereon for releasable connection to an inserter shaft; the body having first and second opposite and parallel planar sides; the hole extending from the first side to the second side; each of the sides being provided with a rounded entryway leading to the hole, such that the hole is devoid of edges against which the suture can impinge.

In still another form of the invention, the suture anchor can comprise a substantially wedge-shaped body having a smaller distal end and larger proximal end, means thereon for retaining a suture, and means thereon for releasable connection to an inserter shaft; the body distal end being of rounded configuration; a plow surface of the body being of rounded configuration in plan view; an abutment surface of the body opposite from the plow surface being of rounded configuration in plan view; and the abutment surface and a boundary surface of the body intersecting to form, in side elevational view, a rounded configuration; the rounded configurations being operable to guide entry of the body into the bore in the bone and to center the body in the bore.

And in yet another form of the invention, the suture anchor can comprise a substantially wedge-shaped body having a smaller distal end and a larger proximal end, the body defining a hole therethrough for retaining a suture, and the body having means thereon for releasable connection to an inserter shaft; the hole being substantially elliptical in width-wise cross-section and having a major axis substantially normal to a minor axis; the major axis being aligned with a selected region of the body to direct stress from the suture toward the selected region of the body.

In another form of the invention, the suture anchor can comprise a substantially wedge-shaped body having a smaller distal end and a larger proximal end, the body defining a hole therethrough for retaining a suture, and the body having means thereon for releasable connection to an inserter shaft; the body having first and second opposite sides; the hole extending from the first side to the second side; each of the sides being provided with a pathway extending from the hole to a boundary surface of the body, the pathway extending into the side of the body further than the diameter of the suture, such that the suture in the hole extends through the pathways and is disposed in the pathways removed from outer surfaces of the body first and second sides.

And in another form of the invention, the suture anchor can comprise a substantially wedge-shaped body having a smaller distal end and a larger proximal end, the body having means thereon for retaining a suture, and a boundary surface having means therein for releasable connection to an inserter shaft; the means for releasable connection to an inserter shaft comprising a smooth-walled counterbore in the boundary surface, and a second bore in a bottom of the counterbore, the second bore being adapted to receive a threaded end portion of the inserter shaft and to be threadedly engaged thereby, and the counterbore being adapted to receive a cylindrically-shaped flexible tip portion of the inserter shaft; wherein flexing of the inserter shaft tip portion is permitted by the counterbore substantially without disturbing the engagement of the threaded end portion of the inserter shaft with the second bore.

The invention also comprises an installation tool for placing a suture anchor and a suture attached thereto in a bore in a bone, the tool comprising an elongated shroud having therein an internal opening; an inserter shaft slidably disposed in the internal opening; the suture anchor being releasably connected to a distal end of the inserter shaft; the shroud being of elastomeric material and configured to form first and second channels on opposite sides of the internal opening and adapted each to retain a portion of the suture attached to the anchor and extending proximally therefrom; each of the channels being formed such that a first portion of the channel at an outer surface of the shroud is narrower than a second portion of the channel spaced from the shroud outer surface; the suture portions being removable from the channel second portions by passing through the channel first portions, the elastomeric material deforming to allow the passage through the channel first portion.

The invention also comprises a bone anchor system comprising a suture anchor having means thereon for releasable connection to an installation tool; and the installation tool for placing the suture anchor and a suture attached thereto in a bore in a bone, the installation tool comprising an elongated shroud having an internal opening, and an inserter shaft slidably disposed in the internal opening, the inserter shaft comprising a proximal rigid portion connected to a distal flexible portion, the distal flexible portion being adapted to releasably connect to the suture anchor.

In another form of the invention, the bone anchor system comprises a suture anchor comprising a substantially wedge-shaped body having a smaller distal end and a larger proximal end, means thereon for retaining a suture, and a boundary surface having means thereon for releasable connection to an inserter shaft; a suture connected to the anchor by the suture retaining means; and an inserter shaft connected to the anchor by the boundary surface inserter shaft connection means, the inserter shaft comprising an elongated rod having a handle at a proximal end thereof and the anchor disposed at a distal end thereof, the handle being generally of a "T" configuration in which the head of the "T", is angled 5°–45° off normal to the axis of the rod, the handle being configured such that the head of the "T", fits a palm of an operator's hand and a portion of the head of the "T" extending outwardly and distally from the rod proximal end is adapted to receive a thumb of the hand of the operator.

In still another form of the invention, the bone anchor system comprises a plurality of suture anchors, each comprising a substantially wedge-shaped body having a smaller distal end and a larger proximal end, means thereon for retaining a suture, and means thereon for releasable connection thereof to an inserter shaft; an inserter shaft connected to each of the anchors by the releasable connection means; and a suture connected to each of the anchors by the suture retaining means, the sutures each being visually distinguishable from the remainder of the sutures, such that appropriate pairs of strands of the sutures may be visually identified by an operator.

In yet another form of the invention, the bone anchor system comprises a suture anchor comprising a substantially wedge-shaped body having a smaller distal end and a larger proximal end, means thereon for retaining a plurality of sutures, and means thereon for releasable connection thereof to an inserter shaft; an inserter shaft connected to the anchor by the releasable connection means; and a plurality of suture strands connected to the anchor by the suture retaining means, the suture strands being visually distinguishable from each other, such that appropriate pairs of strands of the sutures may be visually identified by an operator.

In another form of the invention, the bone anchor system comprises a bone anchor having means thereon for retaining a suture; and the suture retained by the bone anchor; the suture being identifiable by color such that the suture can be distinguished from other sutures of other colors.

The present invention also comprises a method for disposing a suture anchor in a bore in a bone, comprising the steps of:

providing a suture anchor having thereon means for connecting a suture thereto, means for releasably connecting an inserter shaft thereto, a biting edge thereon, and a rounded cam surface on an opposite side of the anchor from the biting edge, the inserter connecting means being offset from a center of the anchor; and providing an inserter shaft comprising an elongated rod having a handle at a proximal end thereof and at a distal end thereof connected to the anchor by the releasable connecting means; and connecting a suture to the anchor by way of the means for connecting a suture to the anchor;

by manipulation of the inserter shaft, inserting the anchor in the bone with the biting edge adjacent a first wall portion of the bore in the bone and the rounded cam surface adjacent an opposite second wall portion of the bore;

pulling the inserter shaft so as to cause the rounded cam portion to move along the second wall portion and the anchor to rotate in the bore with the anchor biting edge biting into the first wall portion of the bore, whereby to lock the anchor in the bore with the suture extending from the bore; and disengaging the inserter shaft from the anchor.

BRIEF DESCRIPTION OF THE DRAWINGS

The invention will now be described with reference to the accompanying drawings wherein;

FIG. 40 is an edge view of the suture anchor shown in FIG. 37;

FIG. 42 is a proximal end view of the suture anchor shown in FIG. 37;

FIG. 43 is a top view of the suture anchor assembly shown in FIG. 35;

FIG. 44 is a side view of the main shaft component of the installation tool associated with the suture anchor assembly shown in FIG. 35;

FIG. 45 is a distal end view of the main shaft shown in FIG. 44;

FIG. 63 is a side view showing the distal end of the suture anchor assembly of FIG. 35 approaching a bore hole formed in a bone;

FIG. 64 is a view showing the distal end of the suture anchor assembly of FIG. 35 as the suture anchor is being pushed into the bore hole;

FIG. 65 is a view like that of FIG. 64, except showing the suture anchor fully deployed in the bone hole, with the installation tool having been removed from the bone;

FIG. 67 is a side view showing the suture anchor of FIG. 66 being inserted into a bore hole;

FIG. 68 is a side view showing the suture anchor of FIG. 66 fully set in the bore hole;

FIG. 72 is a perspective view showing another form of suture anchor formed in accordance with the present invention;

DESCRIPTION OF THE PREFERRED EMBODIMENTS

Figure 1:
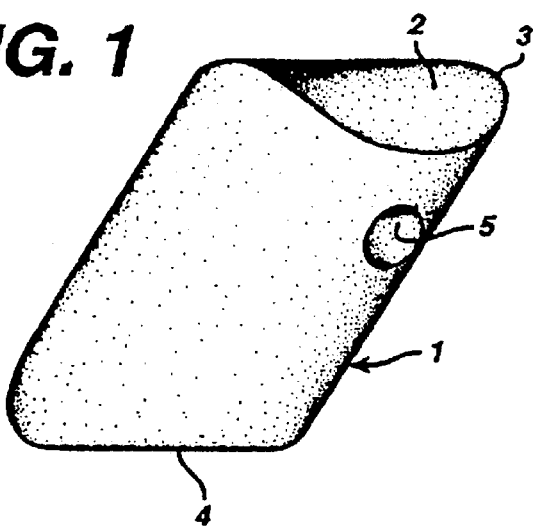
FIG. 1 is a perspective view of a first embodiment of a suture anchor according to the invention.
Figure 2:
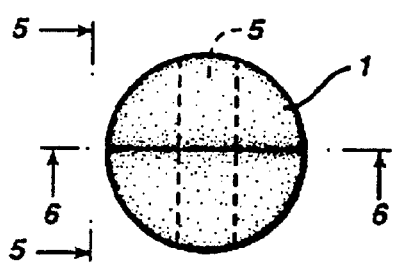
FIG. 2 is an end view of the suture anchor of FIG. 1.
Figure 3:
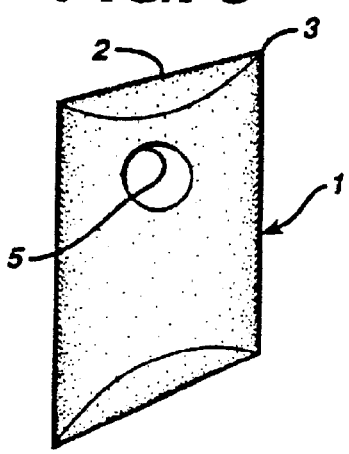
FIG. 3 is a front view of the suture anchor of FIG. 2.
Figure 4:
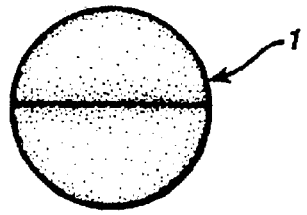
FIG. 4 is an end view of the suture anchor of FIG. 3.
Figure 5:
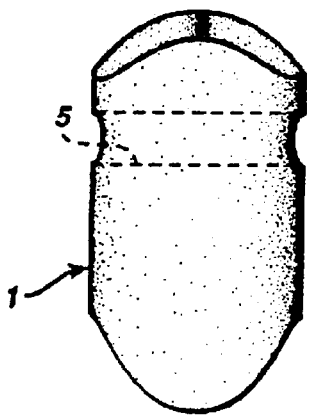
FIG. 5 is a side view of the suture anchor of FIG. 1.
Figure 6:
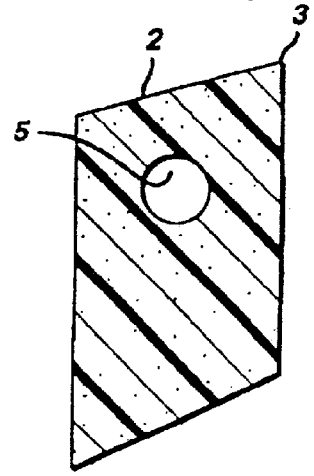
FIG. 6 is a cross-sectional view taken along line 6—6 of FIG. 2.

A first aspect of a suture anchor according to the present invention is a unitized suture anchor, particularly as shown in FIG. 1. The first embodiment of the invention will now be described with reference to the Figures. The suture anchor 1 has a first abutment end 2 and a second abutment end 3. The suture anchor has a substantially cylindrical cross-section as shown in FIG. 2 and the cylindrical longitudinal surface forms with the abutment end 2 a corner 4. The diameter of the suture anchor is sized smaller than the bore hole or opening in the bone receiving the suture anchor. This permits passage of the suture end(s) out of the opening. A suture opening 5 is defined by the body of the suture anchor 1. In an alternative embodiment shown in FIG. 3 the first abutment end 2 and second abutment end 3 are slightly tapered to a point or edge. This is due to the extruding process of formation as will be described below. The suture opening 5 is formed transverse to the longitudinal direction of the suture anchor 1. Also the suture opening 5 is offset from the center of the suture anchor 1 such that an imbalance is formed in the rotation of the device on implantation as described below.

Figure 7:
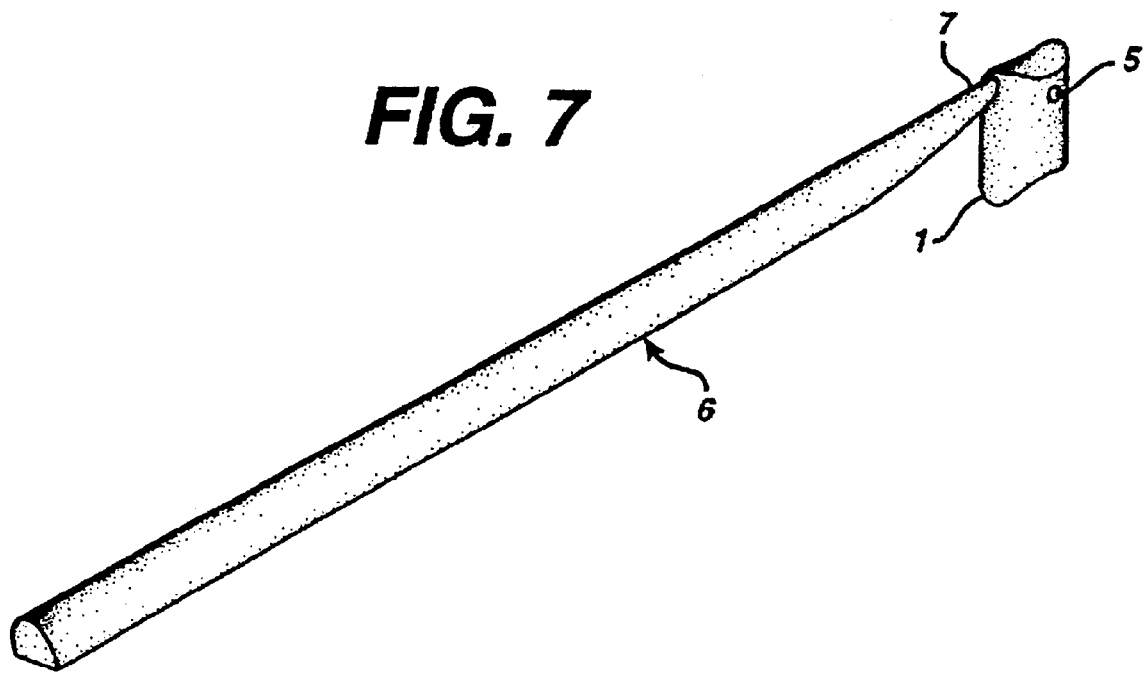
FIG. 7 is a perspective view of the suture anchor and implantation portion of the first embodiment.

The suture anchor may be formed either by extrusion or by injection molding. When injection molding the suture anchor the implantation structure of FIG. 7 is preferred. In that Figure it is seen that a shaft 6 is formed attached to one end of the suture anchor 1. A thinned portion forms a frangible portion 7 which will operate to separate the suture anchor 1 from the shaft 6 upon implantation.

Figure 8:
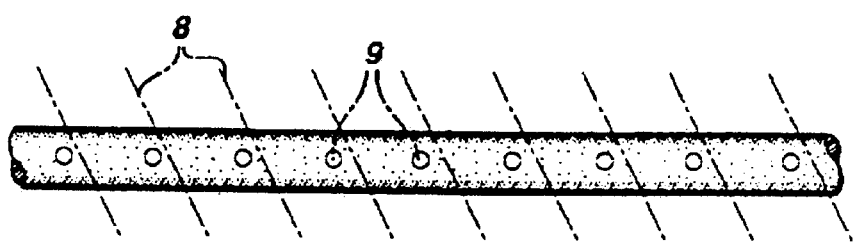
FIG. 8 is a top view of a suture anchor extruded rod blank.

Alternatively, if an extrusion process is used a rod of material is extruded as shown in FIG. 8. Diagonal cuts along cut lines 8 are made after boring openings 9 in the rod at predetermined intervals. Thus, each of the suture anchors is formed by the cut severing the suture body from the suture body of the adjacent anchor.

Figure 9:
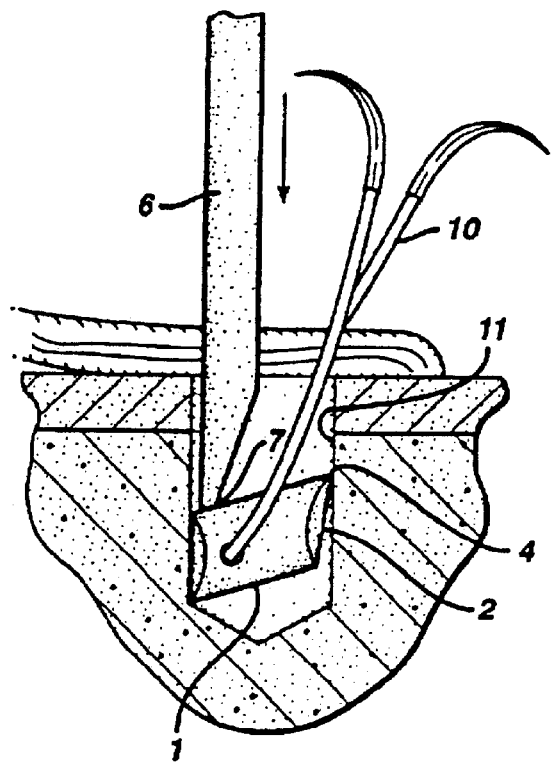
FIG. 9 is a view of the implantation procedure of the present invention.
Figure 10:
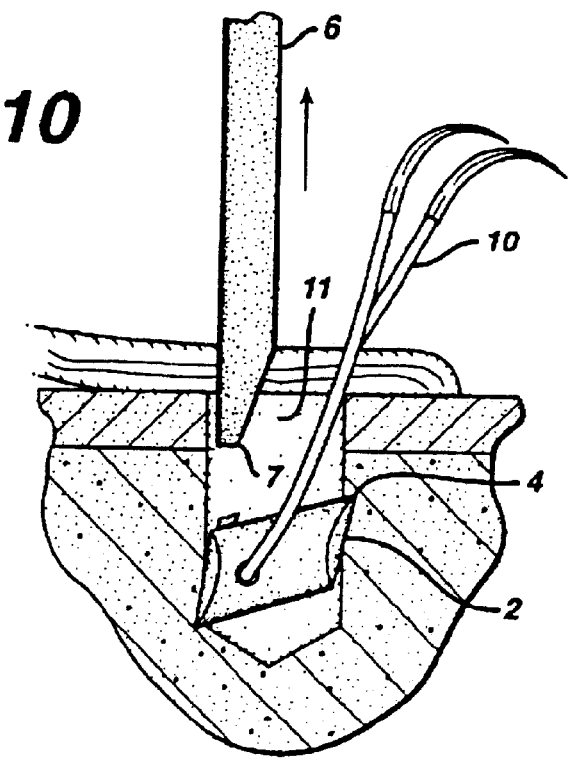
FIG. 10 is a view of the implantation procedure upon removal of the implantation device.

Now an implantation procedure will be described. With reference to FIG. 9 the suture anchor 1 has a suture 10 passed through the opening 5. An appropriate implantation site is created by, for example, boring a hole of predetermined dimension in the bone material slightly larger than the diameter of the suture anchor. The hole may have a diameter of 5 mm for a suture anchor of 3 mm size and is drilled through the outer cortex of the bone into the inner cancellous layer. Upon insertion the suture anchor is placed within the bore hole by the downward motion as shown in FIG. 9. An upward tug on the shaft portion 6 causes a series of events to occur. Initially corner 4 digs into the softer cancellous layer of the bone and second abutment end 3 rotates into engagement with the opposite side of the wall. Thus, the anchor is wedged within the opening of the bore hole 11. The shaft 6 separates from the suture anchor 1 by the breaking of frangible portion 7. This leaves the suture anchor 1 implanted within the bone while the shaft 6 is removed. This securely implants the anchor within the bone material permitting attachment of soft tissue or other materials through the use of suture 10.

Figure 11:
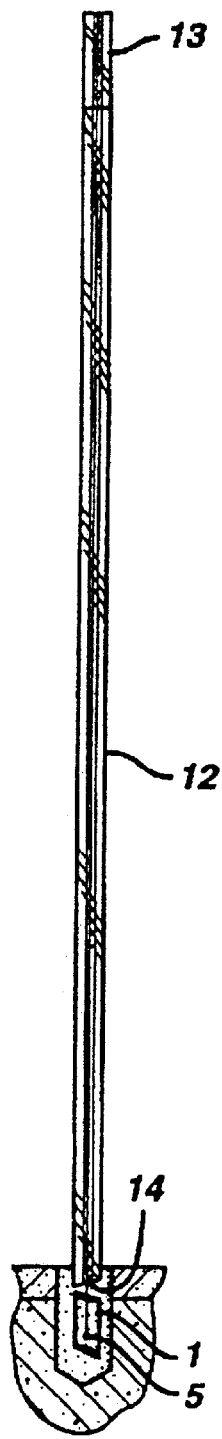
FIGS. 11 and 12 show an alternative implantation procedure for the device of FIG. 1.
Figure 12:
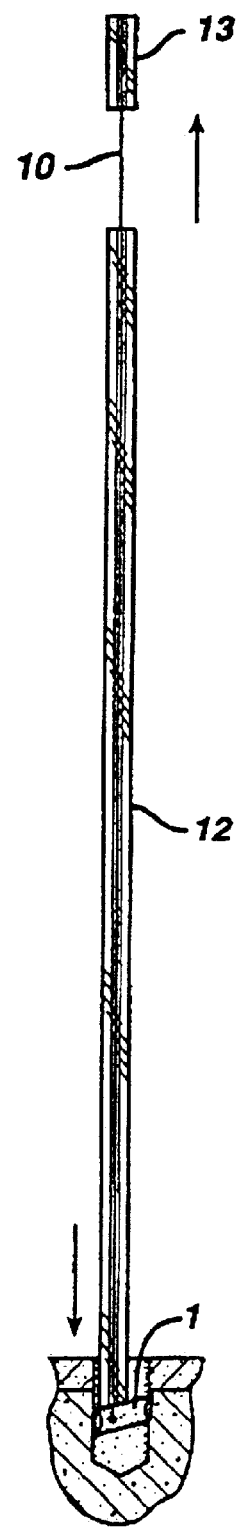
Figure 13:
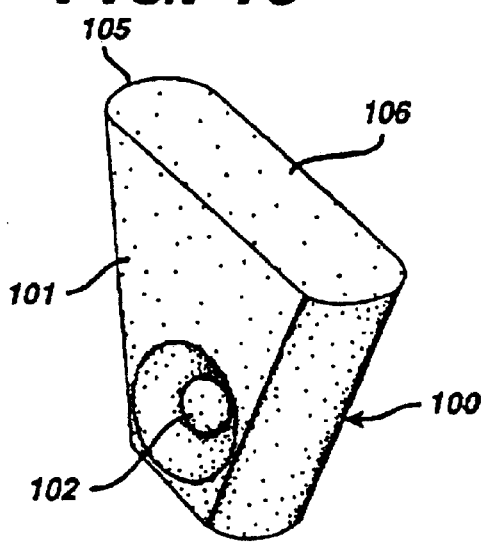
FIG. 13 is a perspective view of an alternate embodiment of the suture anchor of the present invention.

An alternative arrangement for implantation is shown in FIGS. 11 and 12. This arrangement may have the suture already in place such that a preloaded anchor and apparatus is provided. The apparatus includes a tube 12 which may be formed to receive therein the suture anchor 1. The suture 10 is preloaded through the opening 5 defined in the suture anchor and passed up through the tubular portion to a pull tab 13. An appropriate bore hole 11 is prepared in the bone and the suture anchor and tube are inserted therein. The suture anchor is permitted to drop out of the tubular portion and becomes slightly dislocated with respect to the tube. End 14 of the tube is cut at a slight angle in order to promote the rotation of the suture anchor in a particular direction. For example, as shown in FIGS. 11 and 12, the suture anchor is promoted to rotate in a clockwise direction by the longer portion of the tube being on the left side of the figure, that is the longer side of the suture anchor. Once the suture anchor has dropped out of the tube 12, the pull tab 13 is used to snug up the suture anchor within the opening. By pulling upward on the pull tab, the biasing force of the offset hole acting through the pulling force of the suture firmly anchors the suture within the opening. At this point, the pull tab may be removed and the suture slid from within the tubular portion 12.

An embodiment will now be described with reference to FIGS. 13–26. The suture anchor 100 has a body 101 formed in a substantially truncated wedge shape. The body 101 defines a suture opening 102 which is rounded at its openings in order to avoid the likelihood of abrasion to the suture.

An abutment wall 103 may be straight but in the preferred embodiment is provided with a radiused surface which extends in a oblique direction of the anchor. This radius is set to match the radius of the bore hole into which the anchor is intended to be inserted. For example a 4 mm diameter hole would be drilled to receive an anchor with a 4 mm radius to abutment wall 103. A plow wall 104 forms an edge 105 at its intersection with top 106 of the device. The plow wall 104 is also radiused in order to maximize contact between edge 105 and the wall of the bore hole to improve the action of the corner 105 as both a plow and a frictional engagement mechanism for the anchor.

Figure 14A:
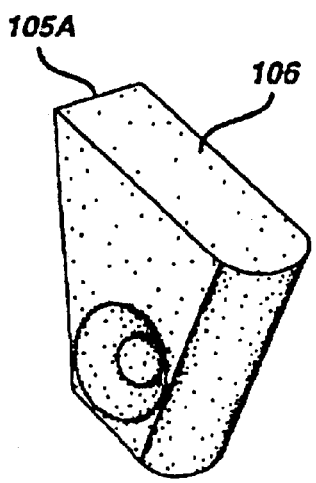
FIGS. 14 a–d show various embodiments of the plow edge of the device of the present invention.
Figure 14B:
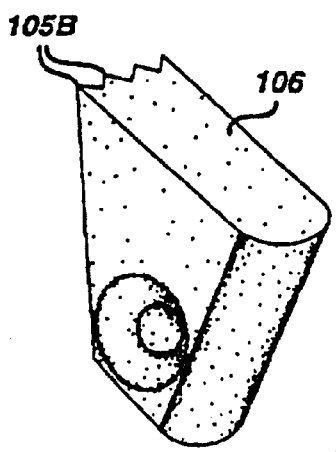
Figure 14C:
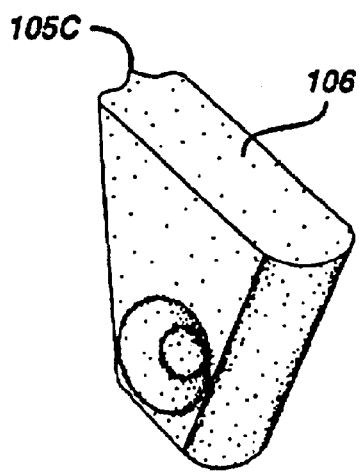
Figure 14D:
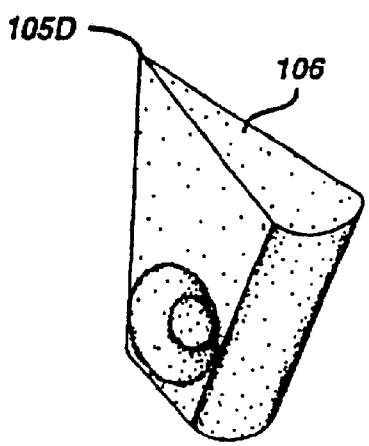
Figure 15:
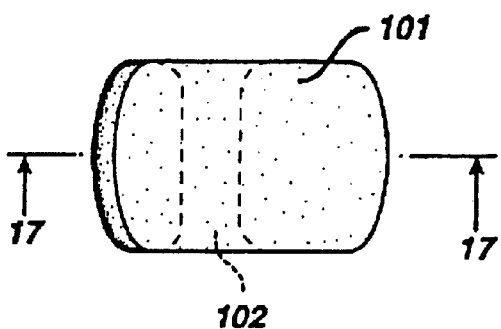
FIG. 15 is a top view of the suture anchor of FIG. 14.
Figure 16:
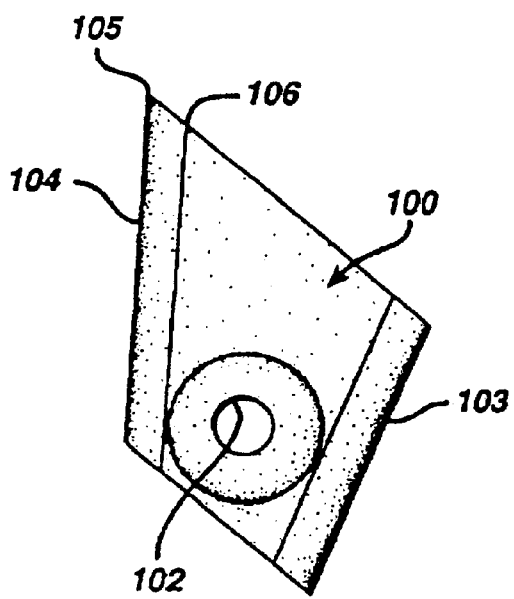
FIG. 16 is a front view of the suture anchor of FIG. 14.
Figure 17:
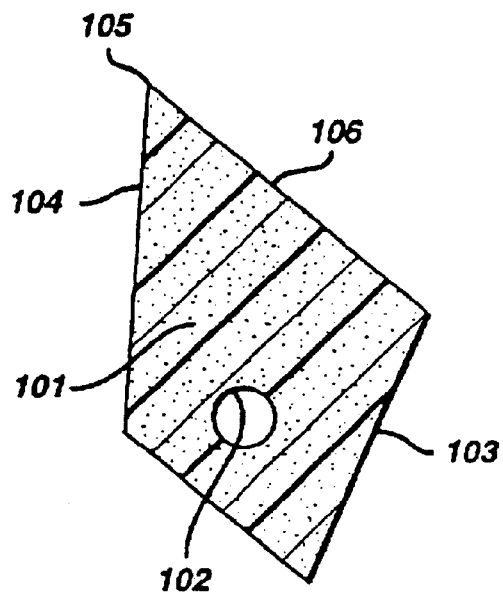
FIG. 17 is a cross-sectional view taken along line 17—17 of FIG. 15.

The corner or edge 105 may be formed in a plurality of manners. For example, the edge 105 (FIG. 14A) may be straight and squared off at the junction between walls 106 and 104, or the edge 105 may be formed with a plurality of teeth 105B to provide additional digging force. Also, the embodiment of FIG. 14B may be modified as shown in FIG. 14C to provide but a single tooth or point which would initiate the digging effect of the edge 105C to introduce the remainder of the edge into the soft cancellous layer. Finally, an additional alternative embodiment is shown in FIG. 14D wherein the edge 105 is actually a point 105D and the plow wall 104 is actually an edge such that the body of the anchor has a substantially conical or cylindrical cross section.

Figure 18:
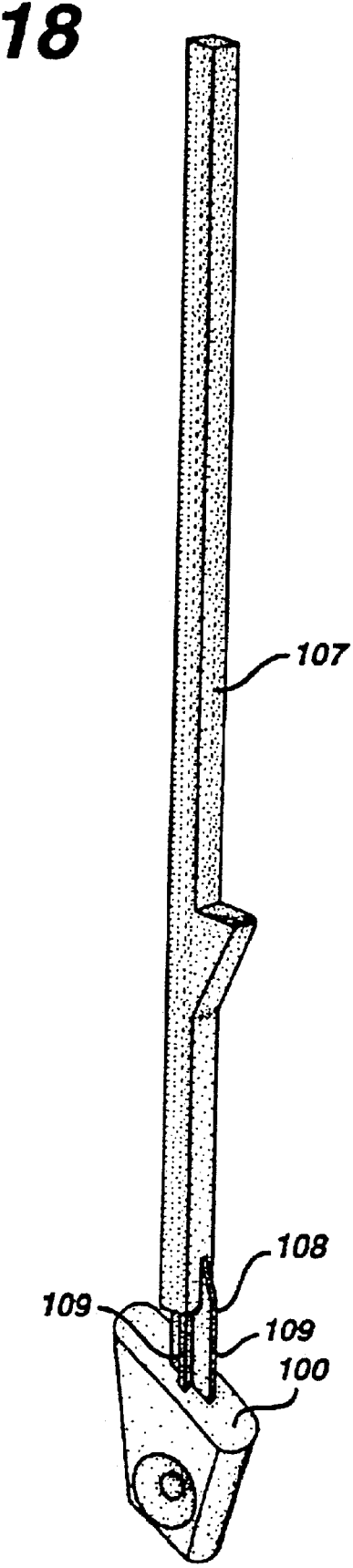
FIG. 18 is a perspective view of the suture anchor of FIG. 14 with a unitized implantation device.

FIG. 18 shows a shaft 107 that extends from the top of the suture anchor prior to insertion of the device into the bore hole. The shaft 107 has formed therein frangible portion 108 in this case formed by a pair of intersecting webs 109. This structure is preferred in the unitized injection molded form of the device as it provides stability between the shaft and suture anchor by maximizing the area moment of inertia of the cross-section while still maintaining a weakness to separation permitting fracture at the frangible portion by minimizing the cross-sectional area.

A stop 110 is provided in order to locate the device in an insertion apparatus prior to implantation. The entire device is injection molded out of a polymer material. The angles of junction for the abutment wall 103 and the top 106 range from about 60° to about 140° and if preferably about 105°. The angle for corner 105 at the juncture of plow wall 104 and top 106 ranges from about 20° to about 90° and preferably about 55°.

The anchors of the present invention may be made from either conventional bioabsorbable materials or conventional non-absorbable materials, combinations thereof and equivalents thereof. Examples of absorbable materials include homopolymers and copolymers of lactide, glycolide, trimethylene carbonate, caprolactone, and p-dioxanone and blends or other combinations thereof and equivalent thereof. Of particular utility are the polylactides, especially poly[L(-)lactide], and the lactide-rich lactide/glycolide copolymers, especially 95/5 poly[L(-)lactide-co-glycolide].

Examples of non-absorbable materials from which the suture anchors of the present invention may be made include metallic biocompatible materials including stainless steel, Nitinol, titanium, Vitalium and equivalents thereof, polymeric materials such as non-absorbable polyesters, polyamides, polyolefins, polyurethanes, and polyacetals and equivalents thereof.

The bonding of the anchors of the present invention to bone may be advantageously increased by promoting bone growth. This can be accomplished by having a microporous surface into which the bone can rapidly grow to aid fixation. This may be particularly advantageous in the case of a metallic anchor, especially a titanium or titanium alloy anchor, but may also provide benefit in the case of polymeric anchors of the present invention, especially those made of absorbable materials. Other methods include the coating of the anchor's surface with a substance to promote adhesion to the bone. Such coatings include the hydroxyapatite-containing-glass coatings described by Ishikawa, et al., in the article "Effect of Hydroxyapatite Containing Glass Coating on the Bonding between Bone and Titanium Implants" appearing in Clinical Materials, Volume 14, 1993, pages 277–285.

It is further noted that the anchors of the present invention can be made to contain growth factors, especially bone growth factors, that can advantageously increase the effectiveness of the anchors, especially in the area of fixation. This may be accomplished in a number of ways, including via coatings or, in the case of absorbable materials, by incorporating the growth factors within the device and allowing them to diffuse out.

The suture anchor devices of the present invention, when made form an absorbable material, are preferably manufactured by molding using conventional injection molding equipment and conventional injection molding processes. A typical molding process includes the steps of (1) injecting a suitable polymer melt into an appropriately designed mold or cavity at process conditions conventionally employed for such polymer systems, (2) releasing from the mold, after the melt cools in the mold, polymer shaped in the proper configuration to meet the design criteria of the device. Additionally the anchor molded from the absorbable polymeric material may be advantageously subjected to an annealing process to increase its mechanical or biological performance. Thermal annealing can also be used to increase the dimensional stability of molded parts by increasing the crystallinity levels in the parts. One or more surgical sutures, or one or more sutures with surgical needles attached, may be used in combination with the suture anchor and may be assembled prior to sterilization. The device can then be sterilized using conventional methods to render the anchor suitable for surgical applications.

Figure 19:
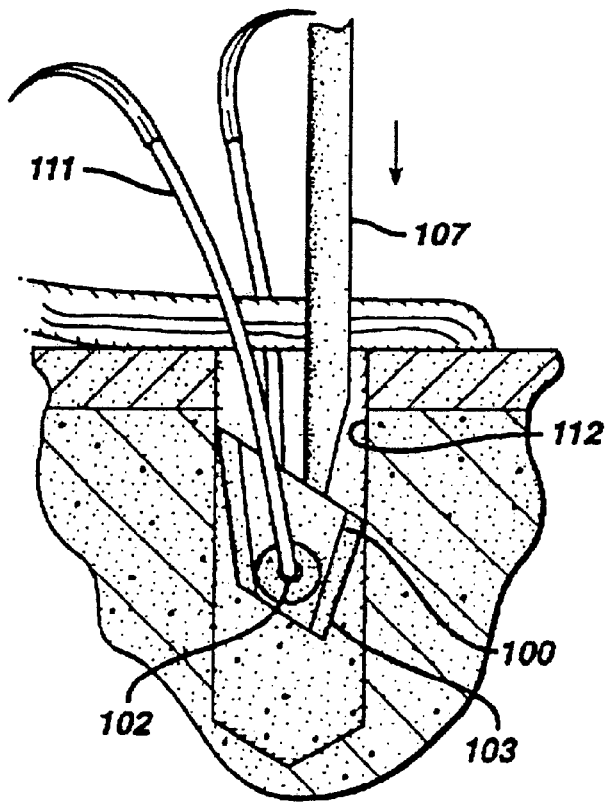
FIGS. 19 through 22 show the implantation procedure of the suture anchor.
Figure 20:
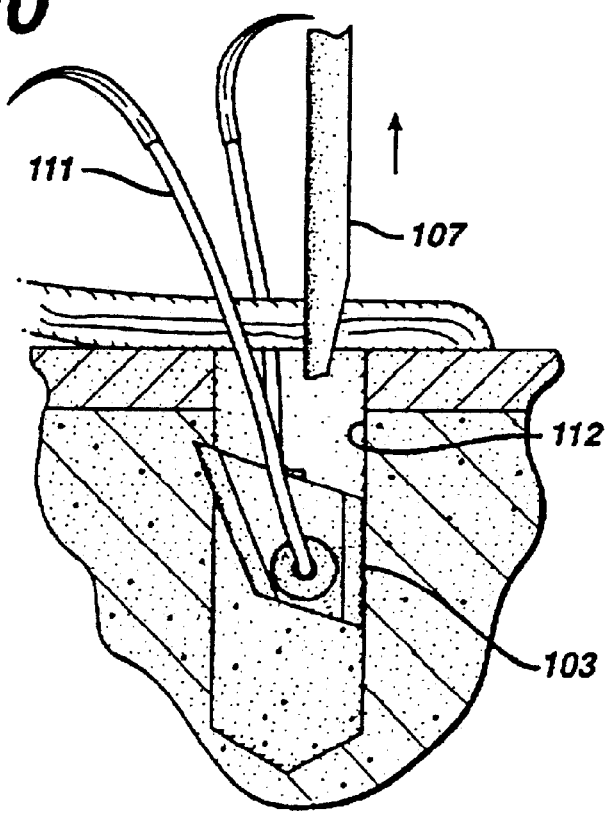
Figure 21:
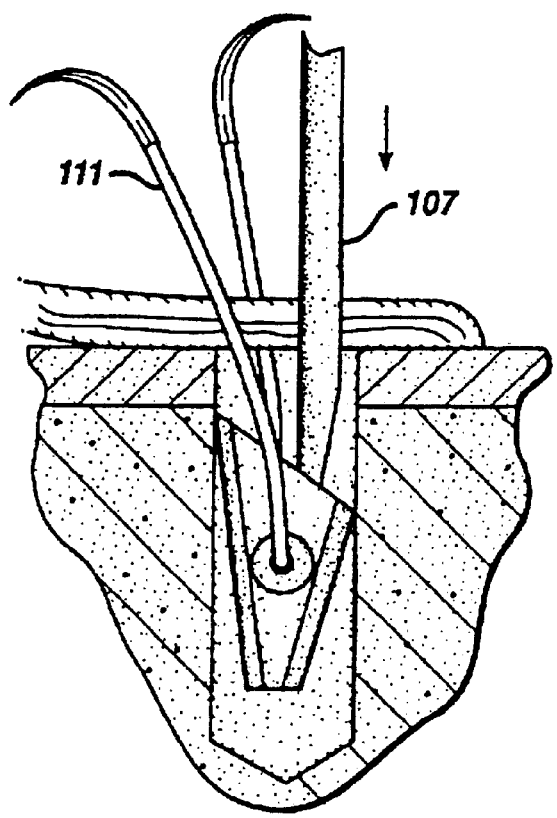
Figure 22:
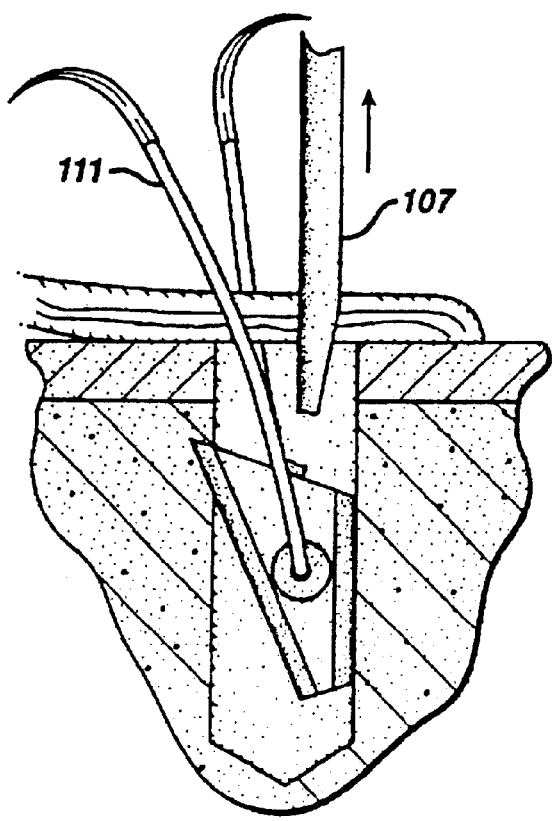

Referring now to FIGS. 19 and 20 the implantation procedure is displayed. Referring to FIG. 19 the suture anchor 100 with shaft 107 attached thereto is inserted into a bore hole after threading of a suture 111 through suture opening 102. The device is inserted gently into the bore hole until the suture anchor is positioned at a desired location in the hole as shown in FIG. 19. It is generally not desired to bottom out the suture anchor. After insertion of the applier (of the type in FIGS. 28 and 29), the shaft is drawn upward forcing the edge 105 to dig into the softer cancellous layer of the bone. The edge digging in on withdrawal of the shaft creates a rotation of the body of the suture anchor which, in combination with the withdrawal tension, breaks the frangible portion 108 and permits removal of the shaft 107 after separation. The suture anchor itself rotates fully until abutment wall 103 is engaged firmly against the surface of the hole 112 formed in the bone. In this case the corner 10 is formed at about a 40° angle between the top 106 and the plow wall 104. Further, abutment wall 103 and top 106 meet to form an angle of about 105°. The top has a length of about 4.6 millimeters and the abutment wall has a length of about 3.2 millimeters and plow wall 104 has a length of about 3.6 millimeters. These dimensions while specific to this embodimemt are proportional in all sizes of the suture anchor being used. That is, a larger suture anchor is made by merely proportionally increasing the dimensions while maintaining the angular relationship of the sides, walls and top in the same configuration. As can be seen in FIGS. 21 and 22, this embodiment can be supplied in a longer version which will require a deeper hole.

Figure 23:
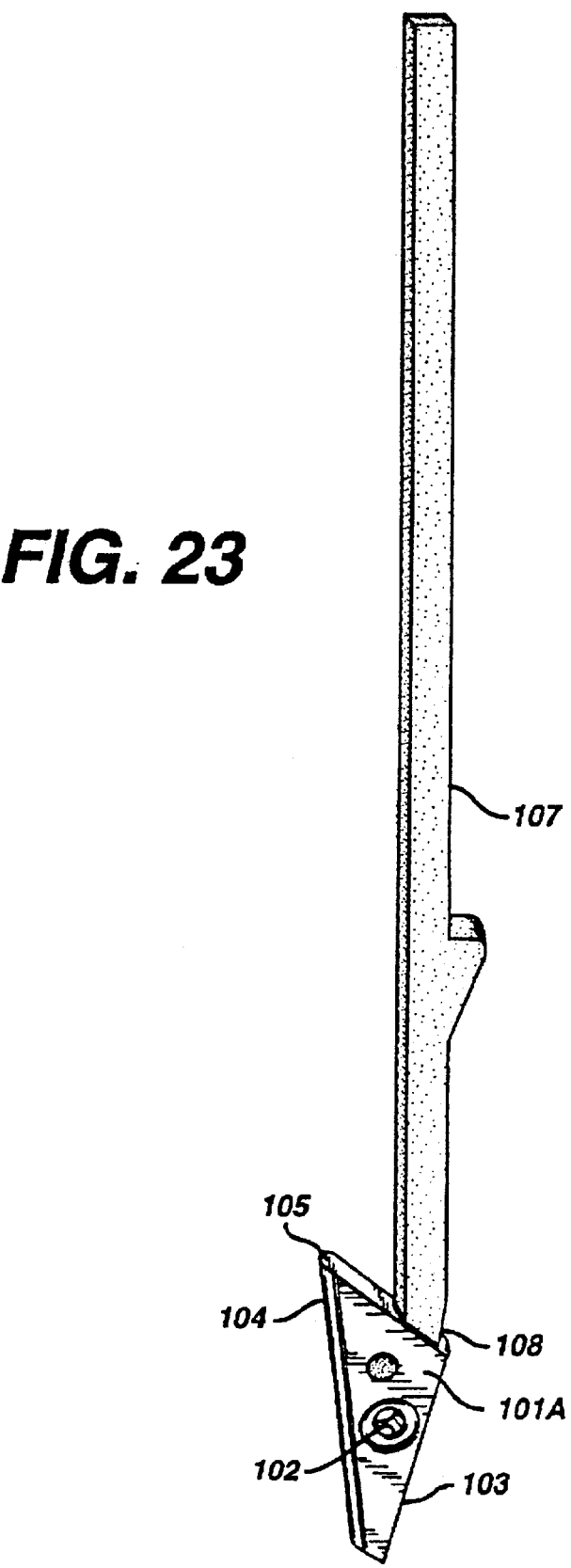
FIG. 23 is a perspective view of a metal suture anchor according to the present invention.

An alternative embodiment as shown in FIG. 23 wherein the body 101A is formed of a metal substance such as a titanium alloy. Preferably the alloy is Ti-6A1-4V alloy. The metal body 101A has a similar suture opening 102 defined therein. An abutment wall 103 and plow wall 104 are provided as in the polymer version of the device and the plow wall 104 forms a corner 105 with the top in a similar fashion. The metal version is provided with a polymer shaft 107 having frangible portion 108 as is provided in the previous embodiment. The metal body 101A is inserted into an injection mold and shaft 107 formed by injection molding the shaft into the metal body 101A. Two intersecting openings are formed to provide a volume to be filled with polymer. The remainder of the metal device is substantially similar to the device of the previous description.

The shaft 107 of the metal version of the anchor may be made of any suitable biocompatible material such as medical grade polymers and may be a bioabsorbable material such as poly[L(-)lactide].

Figure 24:
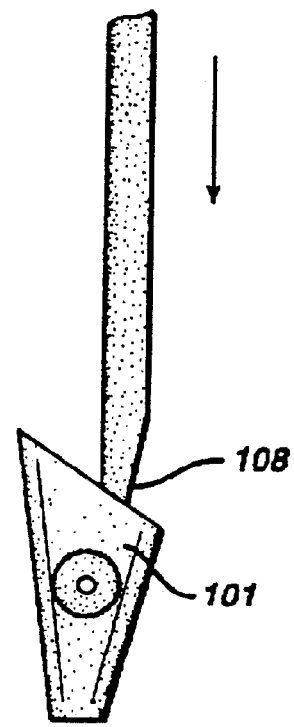
FIG. 24 is a front view of a molded suture anchor according to the present invention.
Figure 25:
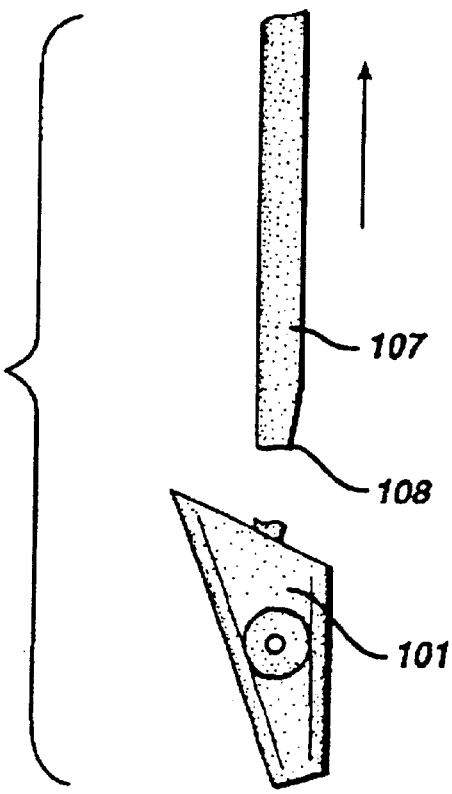
FIG. 25 is a front view of a molded suture anchor according to the present invention after implantation.

FIGS. 24 and 25 show the rotational movement of the body 101 of the suture anchor upon implantation. This rotational movement provides torsional forces to the frangible portion 108 of the shaft 107 to promote the fracture of the shaft at the frangible location.

Figure 26:
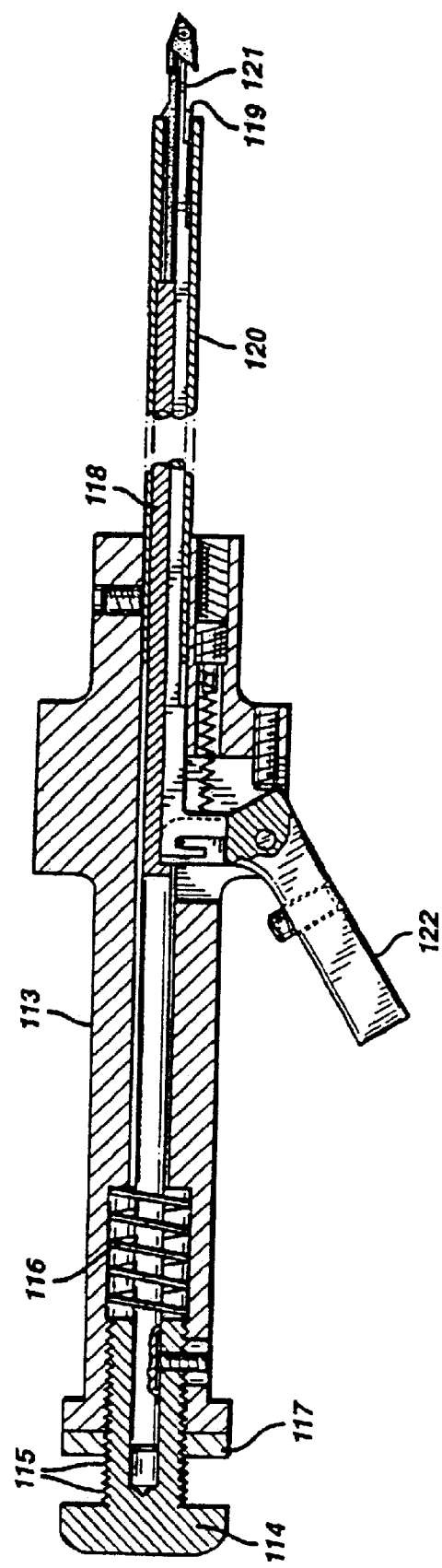
FIG. 26 is an alternative instrument for implanting the suture anchor of the present invention.

A novel insertion mechanism is shown in FIG. 26. The applicator 113 has a screw handle 114 having threads 115 formed thereon. The screw handle is adjusted by rotation against the spring force of spring 116. Once positioned, the screw handle is locked in place using locking ring 117, which is threaded down tightly against the back surface of the applicator 113. A shaft 118 extends from the screw handle 114 along the length of the applicator 113. The shaft has a wedged end 119 which is received substantially within a tubular portion 120 of the applicator. The device may be used in an open procedure. But, tubular portion 120 permits optional insertion of the applicator into a trocar for arthroscopic surgery.

The wedged end 119 is extended from within the tubular portion 120 by the rotation of screw handle 114 to permit extension of the shaft 118 and in particular, the wedge end 119 out of the tubular portion 120. The shaft 107 of the suture anchor is inserted into the tubular portion 120 until the stop 110 seats firmly against the tubular portion 120 of the applicator 113. At this point the screw handle is threaded in the opposite direction in order to draw the wedge end 119 within the tubular portion. The wedging or caming effect of the wedge end 119 firmly grasps the shaft 107 of the suture anchor and holds it within the device.

A finger 121 extends from the end of tubular portion 120 and seats along the top surface of the suture anchor in order to stabilize the body. This prevents premature rotation of the suture anchor and fracture of the frangible portion prior to complete insertion. The finger translates along the longitudinal portion of the tube in response to motion of trigger 122. Upon use the device is inserted into a trocar in order to provide access arthroscopically to the surgical site. The suture anchor is placed into the previously bored bore hole and trigger 122 is manipulated. The manipulation of trigger 122 moves the finger 121 in the longitudinal direction. This forces rotation of the suture anchor body and promotes the fracture of the frangible portion of the shaft while holding the anchor in position. Simultaneously with manipulating the finger 121 the device is withdrawn thus completing the fracture of the frangible portion of the shaft. The previously threaded suture is then used to attach soft tissue according to known surgical procedures.

Figure 27:
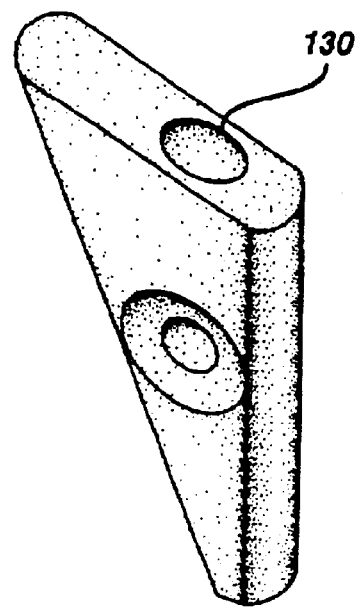
FIG. 27 is a front perspective view of an alternate embodiment of the suture anchor of the present invention.

Referring now to FIG. 27, an alternate and preferred embodiment is shown. The body of the suture anchor is shaped as described above, however a mounting opening 130 is provided at one end of the body of the device. This opening is sized to receive the mounting end 131 of the insertion device shown in FIGS. 28 and 29. The insertion device 132 having mounting end 131 is comprised of an elongated shaft 133. The shaft has two sections, a narrower distal section and a wider proximal section separated by a transitional section 134. The transitional section 134 is conical in shape for reasons which will be described below in connection with the implantation procedure. A handle 135 is provided at the proximal end of the insertion device to facilitate gripping of the device during the implantation procedure.

Figure 28:
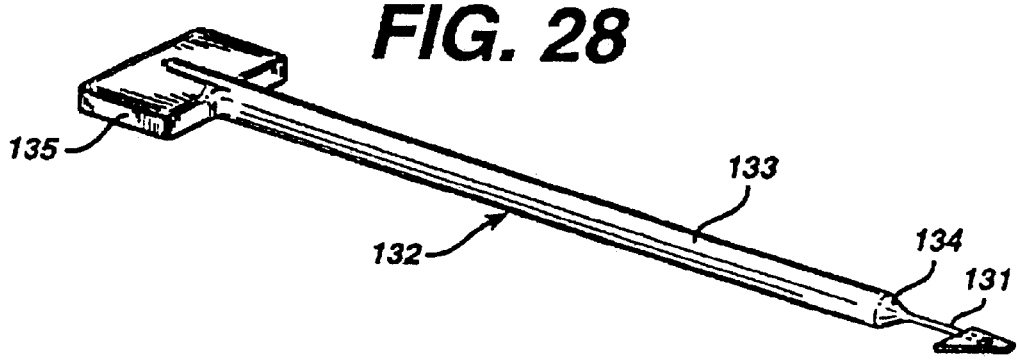
FIG. 28 is a perspective view of an alternate embodiment of the implantation device of the present invention with suture anchor attached.
Figure 29:
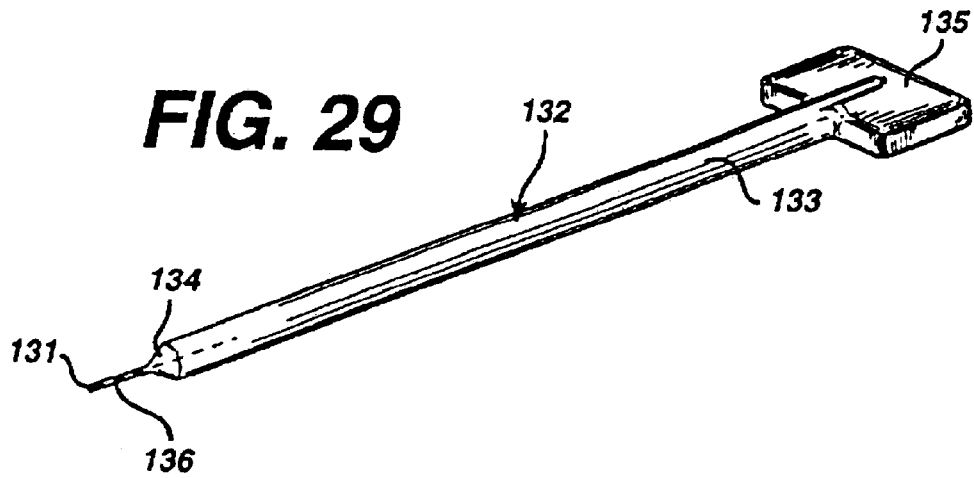
FIG. 29 is a perspective view of the implantation device of FIG. 28.
Figure 30:
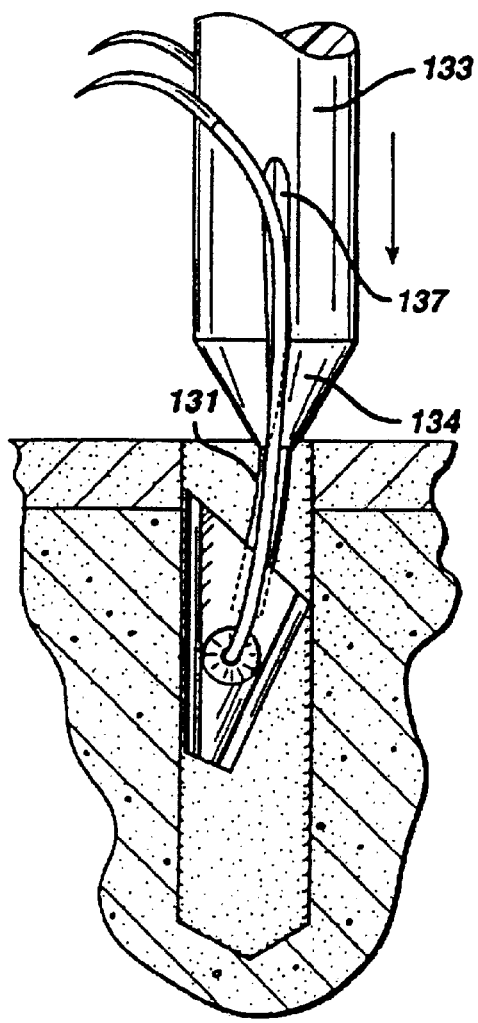
FIG. 30 is a partial cross-sectional view showing implantation of a suture anchor using the device of FIGS. 28 and 29.
Figure 31:
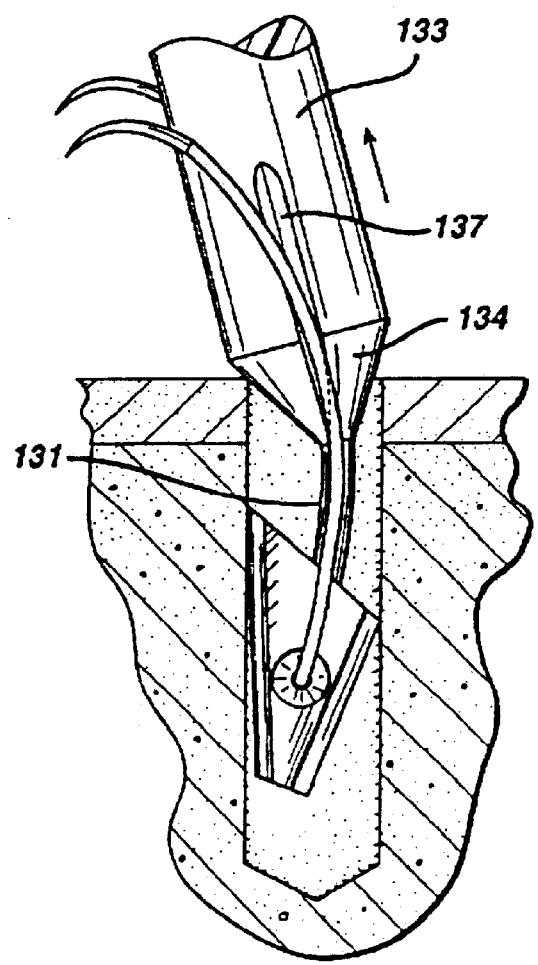
FIG. 31 is a partial cross-sectional view showing implantation of a suture anchor using the device of FIGS. 28 and 29.
Figure 32:
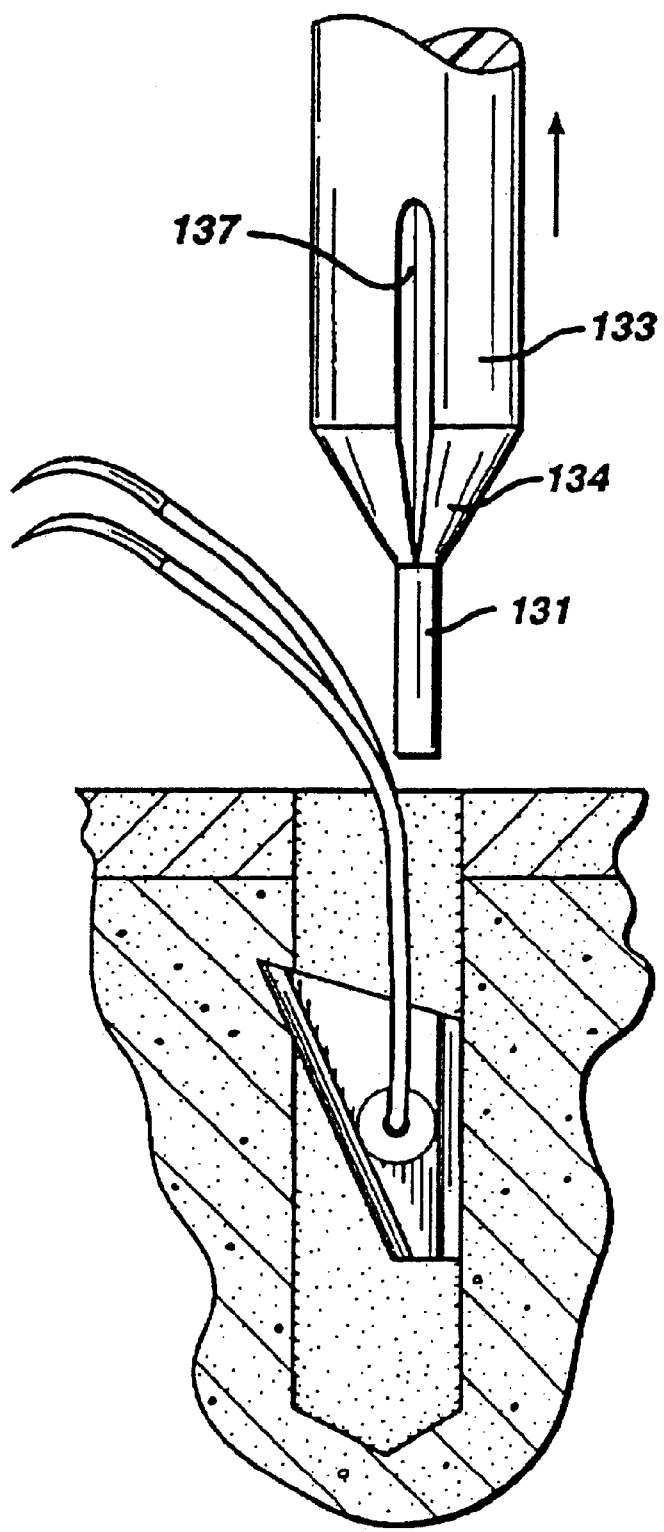
FIG. 32 is a partial cross-sectional view showing implantation of a suture anchor using the device of FIGS. 28 and 29.

In use, (FIGS. 30 and 31) insertion end 131 is received within mounting opening 130 of the body of the suture anchor as shown in FIGS. 28 and 29. Mounting opening 130 is offset from the center line of the body of the suture anchor for reasons which will become apparent below. During the insertion procedure the suture anchor is inserted into a previously-formed bore hole. The insertion tool travels in a position off axis from the hole in the bone. Once the transition portion 134 reaches the top of the bore hole the transition surface forces the insertion tool towards the axis of the bore hole (i.e., the transition portion causes the tool to center). This causes the distal end of the tool to flex slightly and provides additional torque to the suture anchor assisting the plow edge in digging into the bone. A pair of slots 137 are provided to permit the protected passage of the suture out of the bore. Upon removal of the insertion tool, (FIG. 32) the flex of the tool forces the plow edge of the suture anchor into the soft cancellous portion of the bone and the distal tip of the insertion tool slips out of the mounting opening 130 due to the upward force provided on the insertion tool. This provides an extra impetus to the insertion of the suture anchor and its final implantation and mounting.

In an alternative embodiment the insertion tool may be provided with a distal end 136 of a soft polymer material having therein a stiffening member such as a metal wire or polymer of more rigid material. Thus, a soft and manipulable insertion tool is provided having the resilience at the distal end to provide the insertion forces described above. The softer polymer insertion tool aids in producing a friction fit between the distal tip of the insertion tool and the mounting opening 130. Thus, a more sure grip is provided between the tool and the body of the suture anchor.

In general the mounting opening 130 need not be cylindrical in shape. The mounting opening and distal tip of the insertion tool may be shaped so as to prevent rotation of the suture anchor about the tip.

Figure 33:
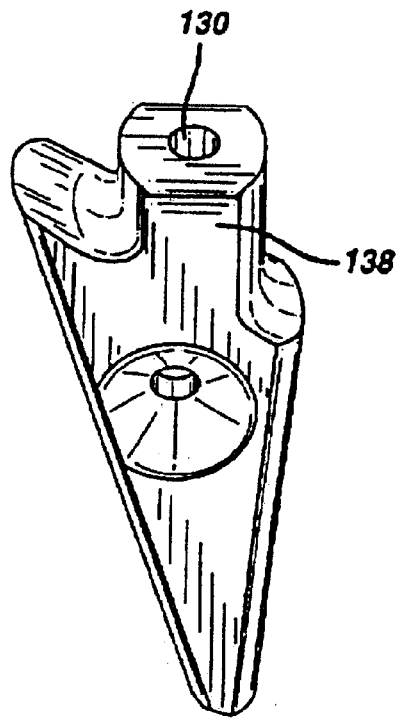
FIG. 33 is an alternate embodiment of the suture anchor of the present invention.
Figure 34:
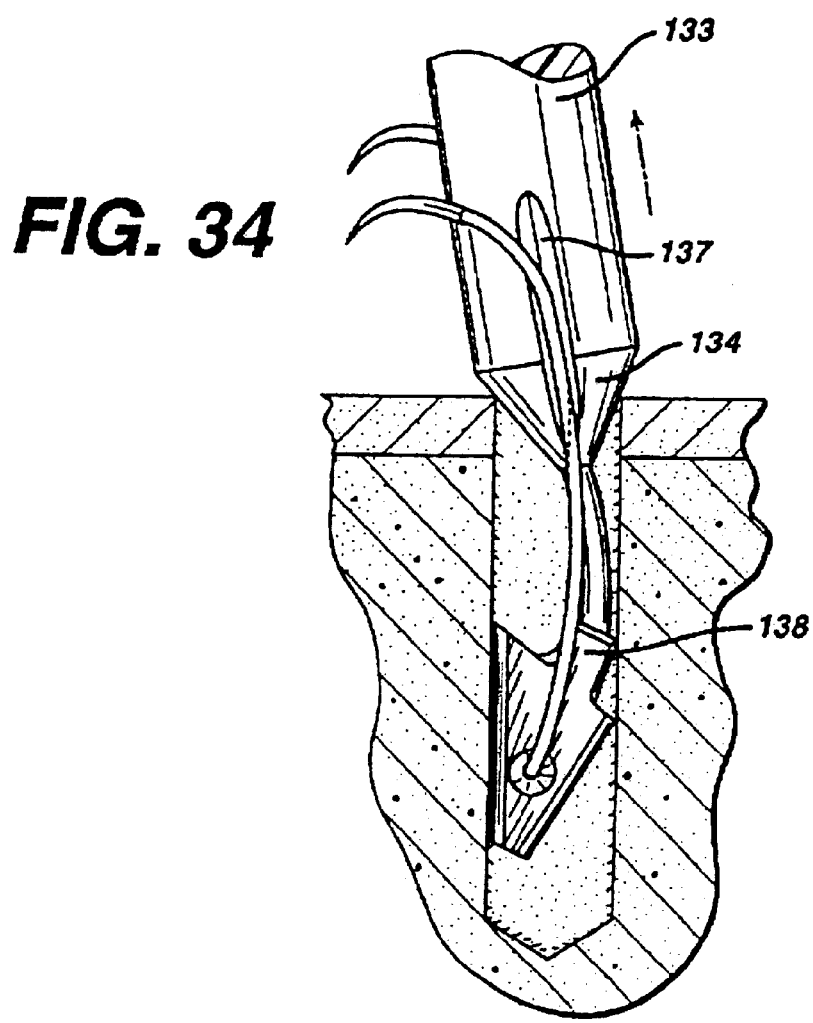
FIG. 34 is a partial cross-sectional view showing implantation of the suture anchor using the device of FIG. 33.

A further embodiment developed for single piece polymer anchors is shown in FIGS. 33 and 34. The anchor has substantially the same shape as the anchors described above, however a protuberance 138 extends from the top surface of the wedge. This protuberance has formed therein the mounting opening 130 which receives the insertion tool described above as shown in FIG. 34. This protuberance provides an area for defining the mounting opening 130 such that the opening is not formed within the body of the wedge, possibly weakening the wedge.

Figure 35:
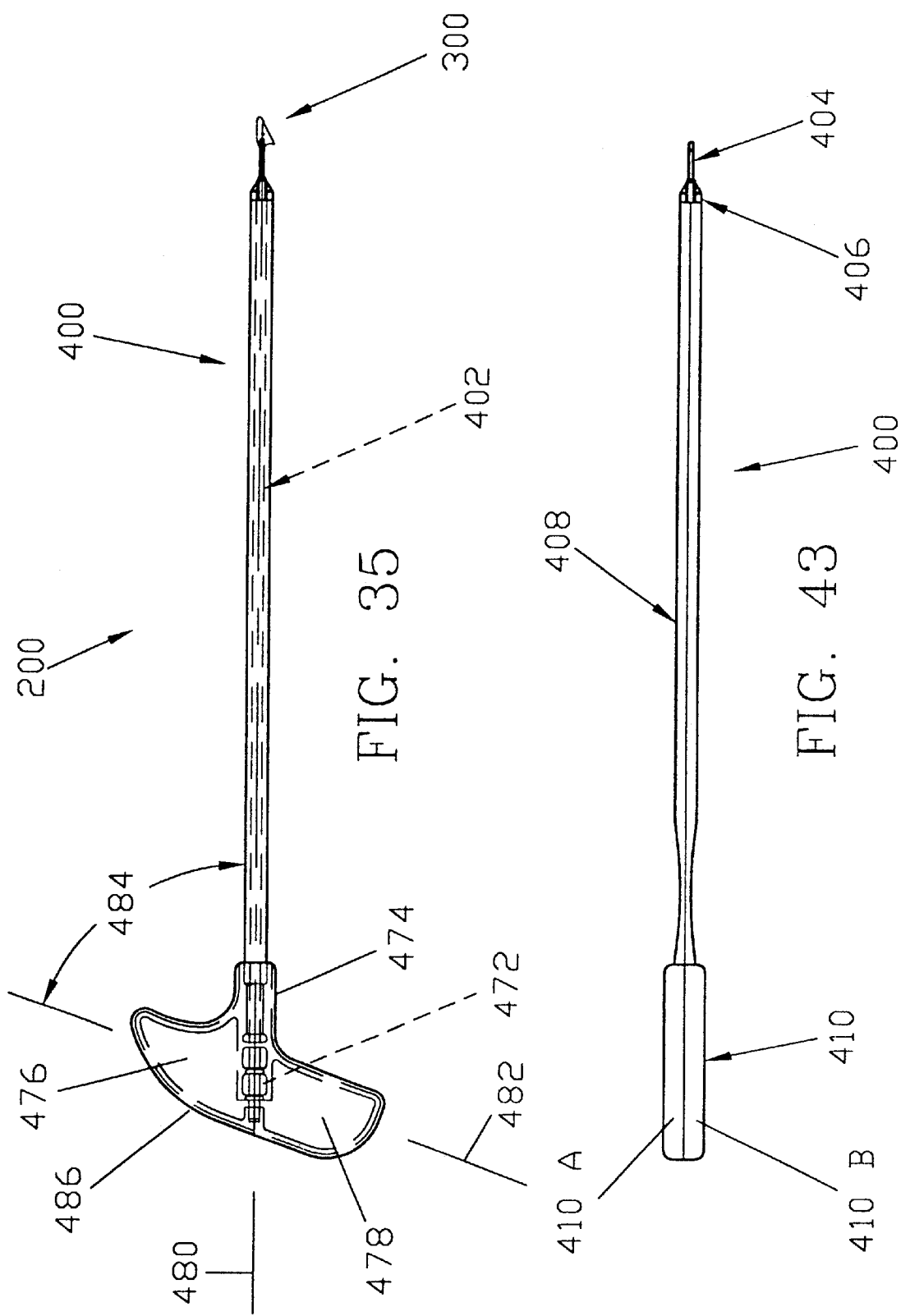
FIG. 35 is a side view of a suture anchor assembly formed in accordance with the present invention.
Figure 36:
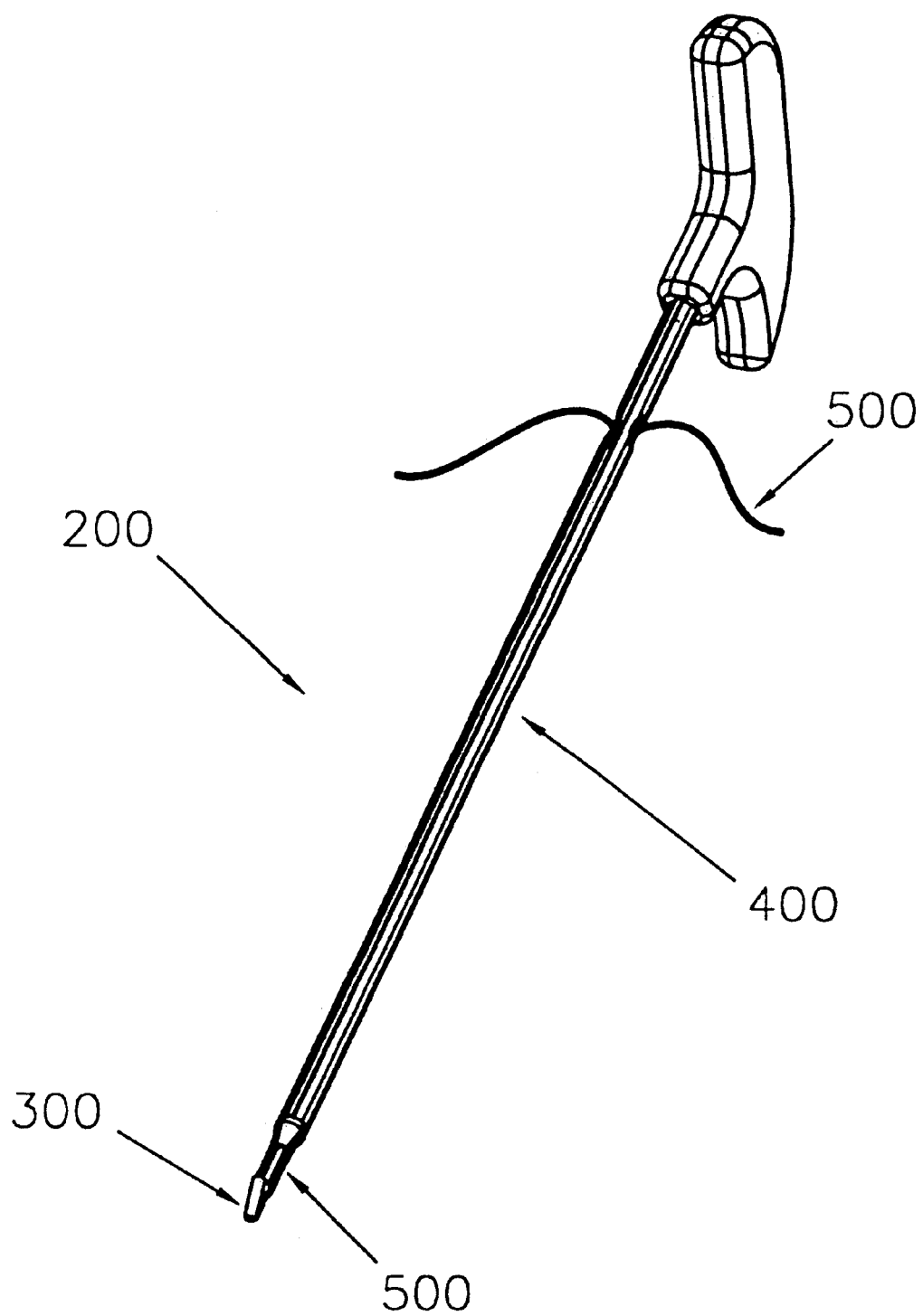
FIG. 36 is a perspective view of the suture anchor assembly shown in FIG. 35.
Figures 37, 59:
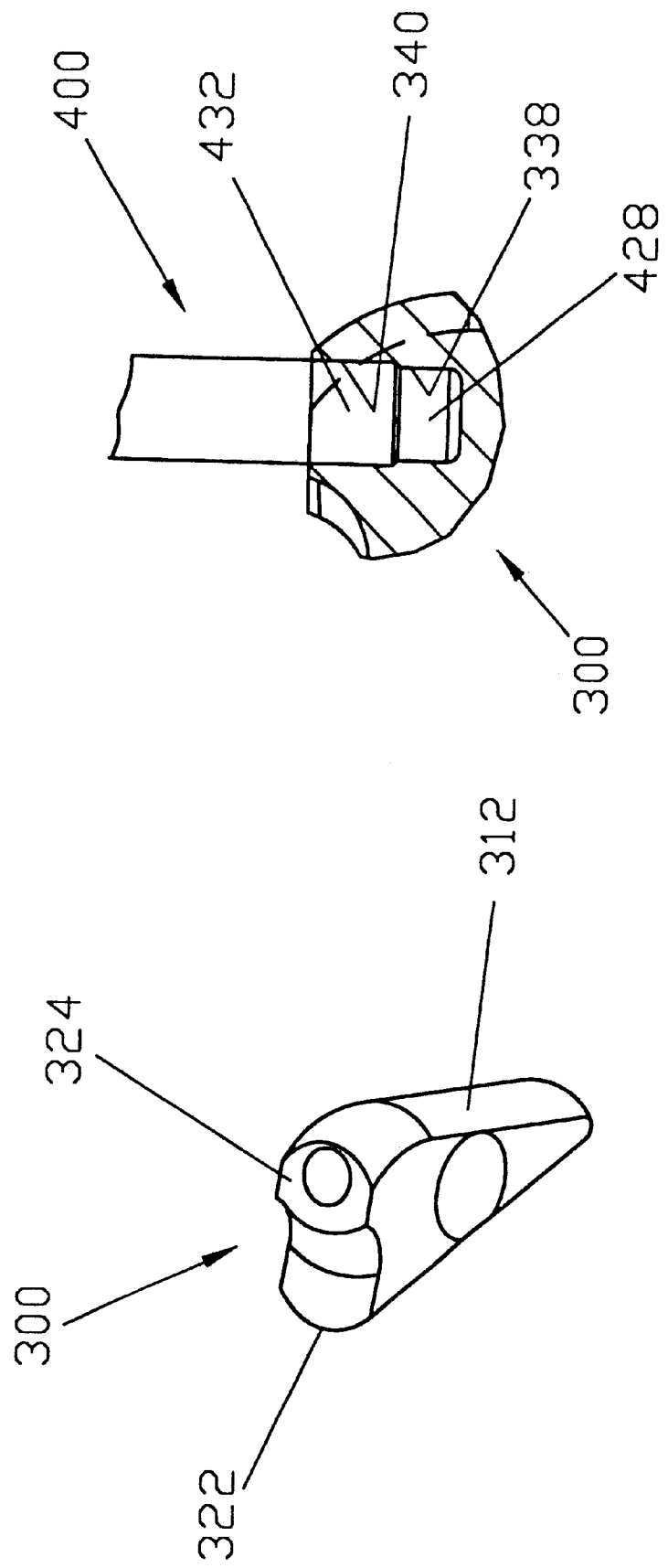
FIG. 37 is a perspective view of the suture anchor associated with the suture anchor assembly shown in FIG. 35.
FIG. 59 is a partial view showing the proximal end of the suture anchor shown in FIG. 37 joined to the distal end of the shaft tip shown in FIG. 46.
Figure 38:
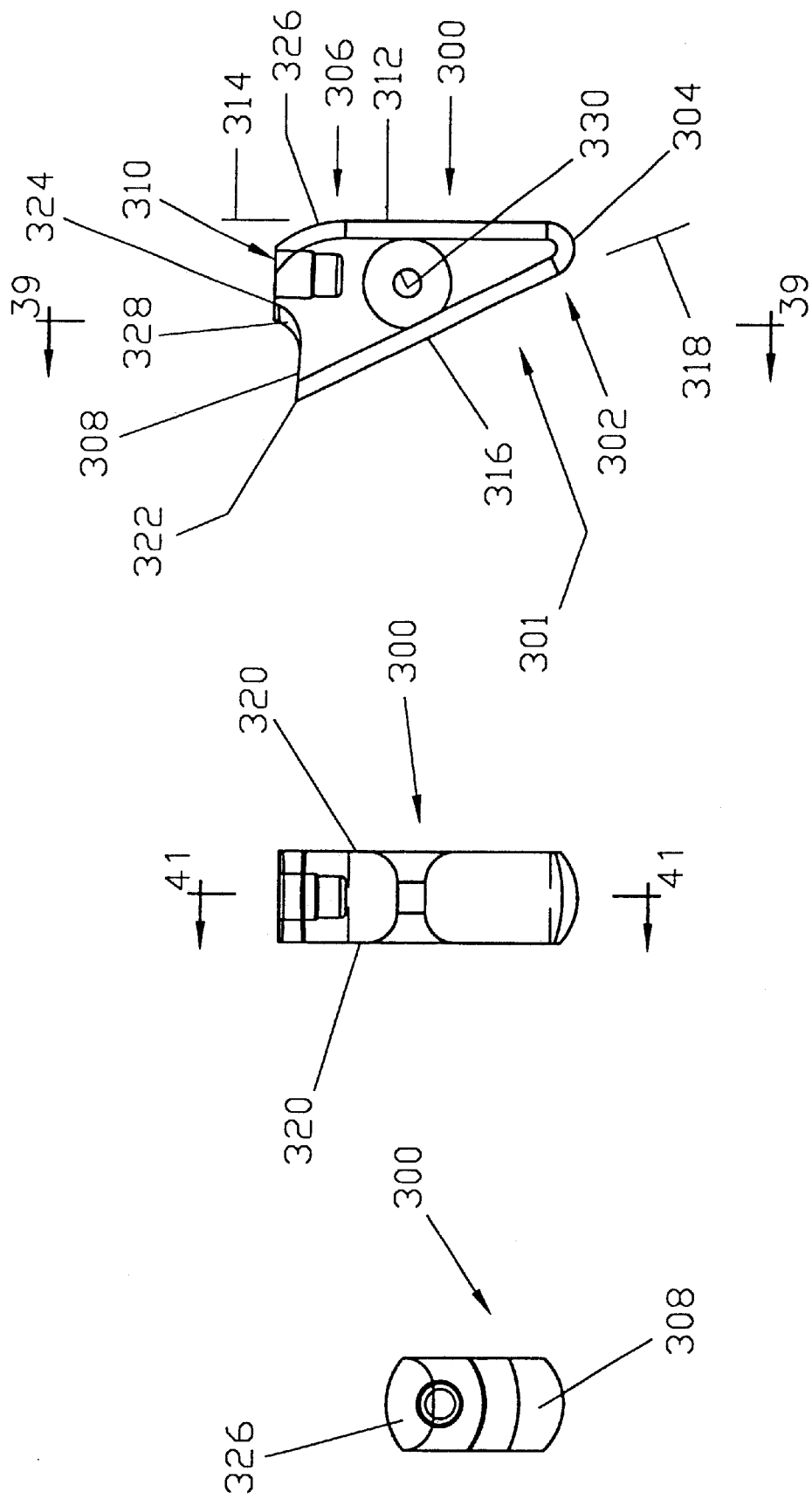
FIG. 38 is a front view of the suture anchor shown in FIG. 37.
Figures 39, 41:
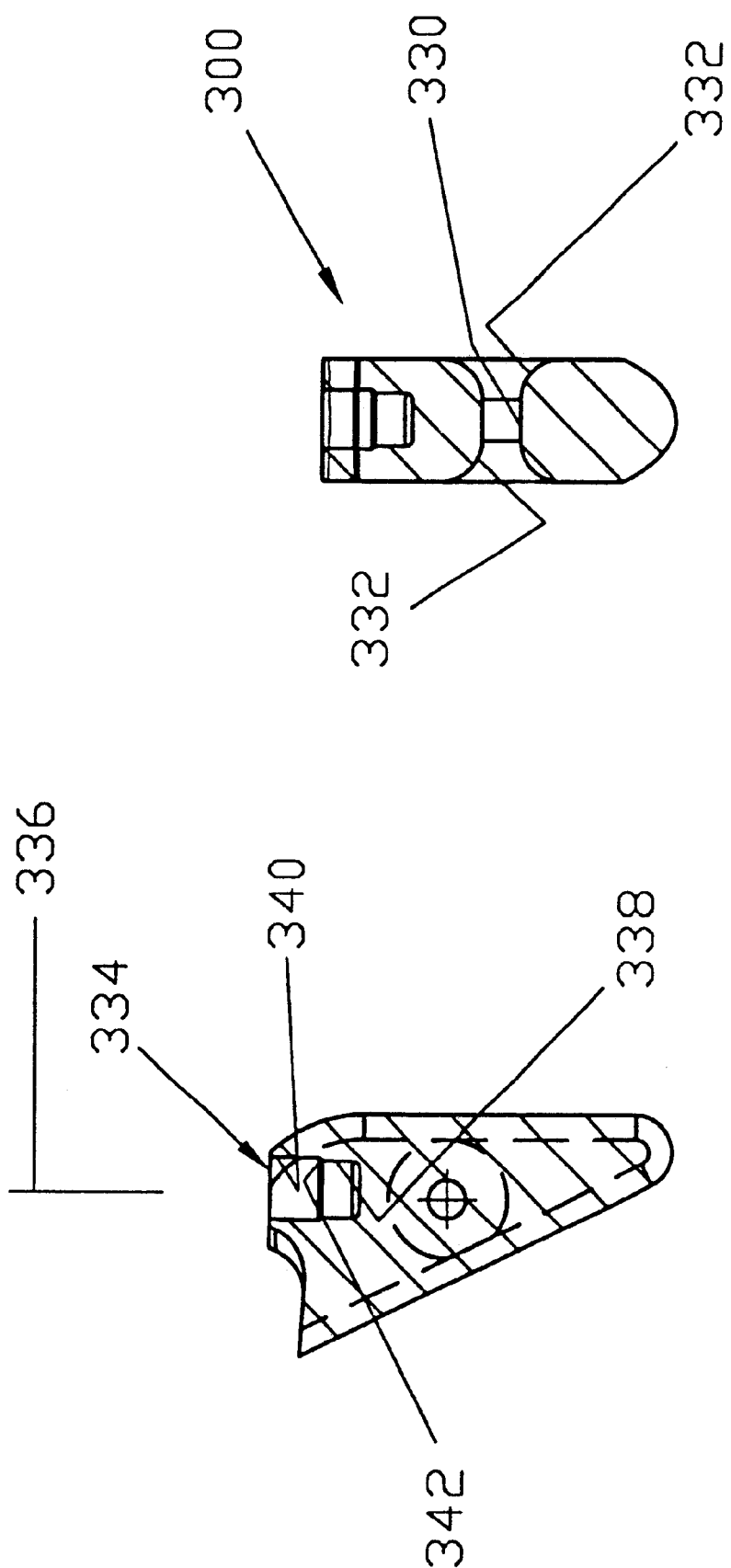
FIG. 39 is a sectional view taken along line 39—39 of FIG. 38.
FIG. 41 is a sectional view taken along line 41—41 of FIG. 40.

Looking next at FIGS. 35 and 36, an alternative and preferred form of suture anchor assembly 200 is shown. Suture anchor assembly 200 generally comprises a suture anchor 300, an installation tool 400 and a suture 500.

Suture anchor 300 is shown in greater detail in FIGS. 37–42. Suture anchor 300 comprises a body 301 having a generally wedge-shaped configuration. Body 301 comprises a relatively narrow distal end 302 terminating in a rounded distal end surface 304, and a relatively wide proximal end 306 terminating in a ledge surface 308 and a protuberance 310. An abutment surface 312 extends along a longitudinal axis 314, and a plow surface 316 extends along an intersecting axis 318. Suture anchor 300 also comprises a pair of side surfaces 320. As seen in the drawings, abutment surface 312 and plow surface 316 extend between the two side surfaces 320 and have a rounded configuration. Preferably this rounded configuration is formed so as to have the same radius of curvature as the bore hole into which the suture anchor is intended to be installed. Plow surface 316 and ledge surface 308 meet in a relatively sharp, well-defined biting edge 322.

Protuberance 310 comprises a substantially flat proximal end surface 324, a cam surface 326 extending between abutment surface 312 and proximal end surface 324, and a transition surface 328 extending between ledge surface 308 and proximal end surface 324. As seen in the drawings, cam surface 326 is curved along its length. Cam surface 326 can be formed with a relatively constant radius of curvature throughout its length or, alternatively, cam surface 326 can be formed so as to have a changing radius of curvature when progressing distally to proximally along its length, for reasons which will be hereinafter discussed. By way of example, cam surface 326 can be formed so as to have a progressively increasing, or a progressively decreasing, radius of curvature when progressing distally to proximally along its length.

The suture anchor's ledge surface 308, transition surface 328, and proximal end surface 324 together form a complete boundary surface 329.

A through-hole 330 extends across suture anchor 300, from one side surface 320 to the other. Through-hole 330 is sized so as to have a diameter somewhat larger than the diameter of suture 500, whereby suture 500 can be slipped through throughhole 330, as will hereinafter be discussed in further detail. If desired, through-hole 330 can be sized so as to have a diameter somewhat larger than the combined diameters of two or more sutures, whereby several sutures can be simultaneously slipped through through-hole 330. Preferably the entryways to through-hole 330 are rounded somewhat as shown at 332 so as to provide a smooth transition between side surfaces 320 and through-hole 330. Such a configuration assists initial passage of suture 500 through through-hole 330, as well as facilitating subsequent slipping motion of the suture relative to the suture anchor, e.g., such as when the suture anchor is deployed in a bone. In addition, such a configuration helps distribute the suture bearing stress more uniformly throughout the contour of through-hole 330.

A blind hole 334 opens on the suture anchor's proximal end surface 324 and extends distally into the suture anchor along an axis 336. Blind hole 334 serves as a mounting opening to receive the distal end of installation tool 400, as will hereinafter be discussed. Blind hole 336 is disposed closer to abutment surface 312 than to biting edge 322. Axis 336 is preferably set at a slightly intersecting angle relative to the longitudinal axis 314 of abutment surface 312. Preferably the axis 336 of blind hole 334 is set at an angle of about 1° relative to the longitudinal axis 314 of abutment surface 312, although this angle may be varied as preferred. Blind hole 334 comprises a bore 338 and a counterbore 340. Bore 338 and counterbore 340 meet at an annular shoulder 342.

Suture anchor 300 can be formed using any of the materials and/or techniques hereinabove discussed in connection with any of the anchors hereinabove discussed, or it can be formed using any other appropriate biocompatible material or technique. In one preferred form of the invention, suture anchor 300 is formed out of a bioabsorbable material such as polylactic acid (PLA).

Looking next at FIGS. 35 and 43, installation tool 400 generally comprises a main shaft 402, a shaft tip 404, a nose 406, a shroud 408, and a handle 410.

Main shaft 402 is shown in greater detail in FIGS. 44 and 45. It comprises a substantially rigid elongated rod having a distal end 412 terminating in a distal end surface 414, and a proximal end 416 terminating in a proximal end surface 418. A blind hole 420 is formed in the distal end of the shaft, extending proximally from distal end surface 414. Blind hole 420 is used to connect main shaft 402 to shaft tip 404, as will hereinafter be discussed. A plurality of circumferentially-extending surface grooves 422 are formed in the proximal end of main shaft 402, just distal to proximal end surface 418. Surface grooves 422 provide the proximal end of main shaft 402 with a contour, and are used to connect main shaft 402 to handle 410, as will also hereinafter be discussed.

Figure 46:
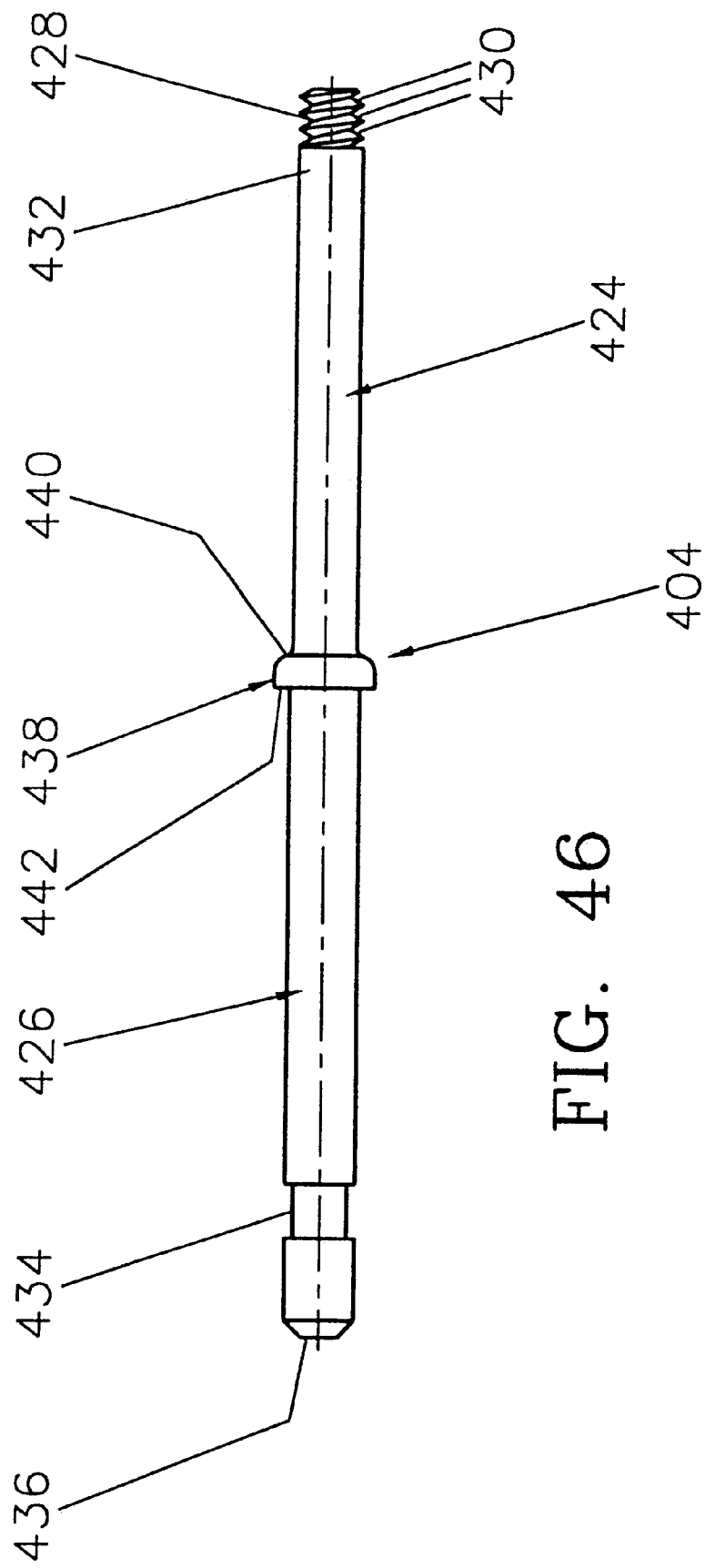
FIG. 46 is a side view of the shaft tip component of the installation tool associated with the suture anchor assembly shown in FIG. 35.
Figure 49:
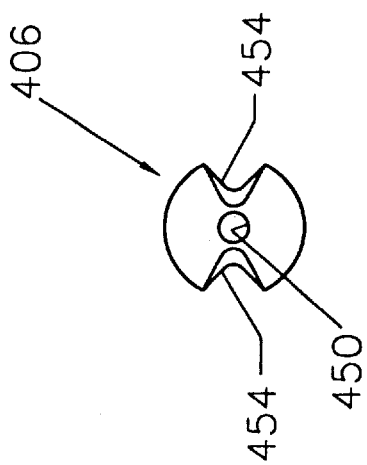
FIG. 49 is a distal end view of the nose shown in FIG. 47.
Figure 47:
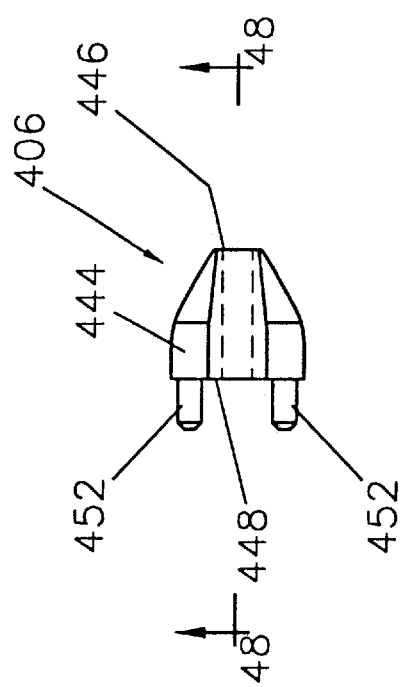
FIG. 47 is a side view of the nose component of the installation tool associated with the suture anchor assembly shown in FIG. 35.
Figure 50:
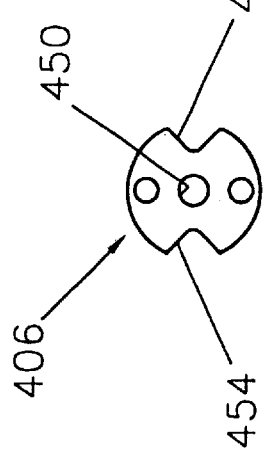
FIG. 50 is a proximal end view of the nose shown in FIG. 47.
Figure 48:
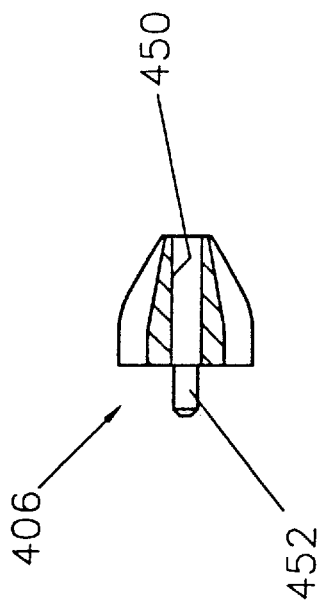
FIG. 48 is a sectional view taken along line 48—48 of FIG. 47.

Shaft tip 404 is shown in greater detail in FIG. 46. It comprises a relatively short rod having a distal end 424 and a proximal end 426. Distal end 424 is formed so as to be somewhat flexible, and terminates in a threaded portion 428 comprising a plurality of screw threads 430. The crests of screw threads 430 have substantially the same diameter as the adjoining portion 432 of shaft tip 404, which diameter is slightly larger than the diameter of the suture anchor's bore 338 but slightly smaller than the diameter of the suture anchor's counterbore 340, for reasons which will hereinafter be discussed. The total length of the shaft tip's threaded portion 428 is sized to be approximately the same as the distance between the suture anchor's shoulder 342 and the base of blind hole 334. A circumferentially-extending surface groove 434 is formed in proximal end 426 of shaft tip 404, just distal to proximal end surface 436. A flange 438 is disposed intermediate shaft tip 404. Flange 438 provides a distally-facing shoulder 440 and a proximally-facing shoulder 442.

Shaft tip 404 can be formed out of any appropriate biocompatible material. By way of example, in one preferred form of the invention, shaft tip 404 is formed out of 17-4 PH stainless steel.

Nose 406 is shown in greater detail in FIGS. 47–50. Nose 406 comprises a generally frustoconical body 444 terminating in a distal end surface 446 and a proximal end surface 448. An axial hole 450 opens on, and extends between, distal end surface 446 and proximal end surface 448. A pair of posts 452 extend proximally out of the nose's proximal end surface 448. A pair of diametrically-opposed surface grooves 454 extend between distal end surface 446 and proximal end surface 448 in the manner shown in the drawings.

Figure 51:
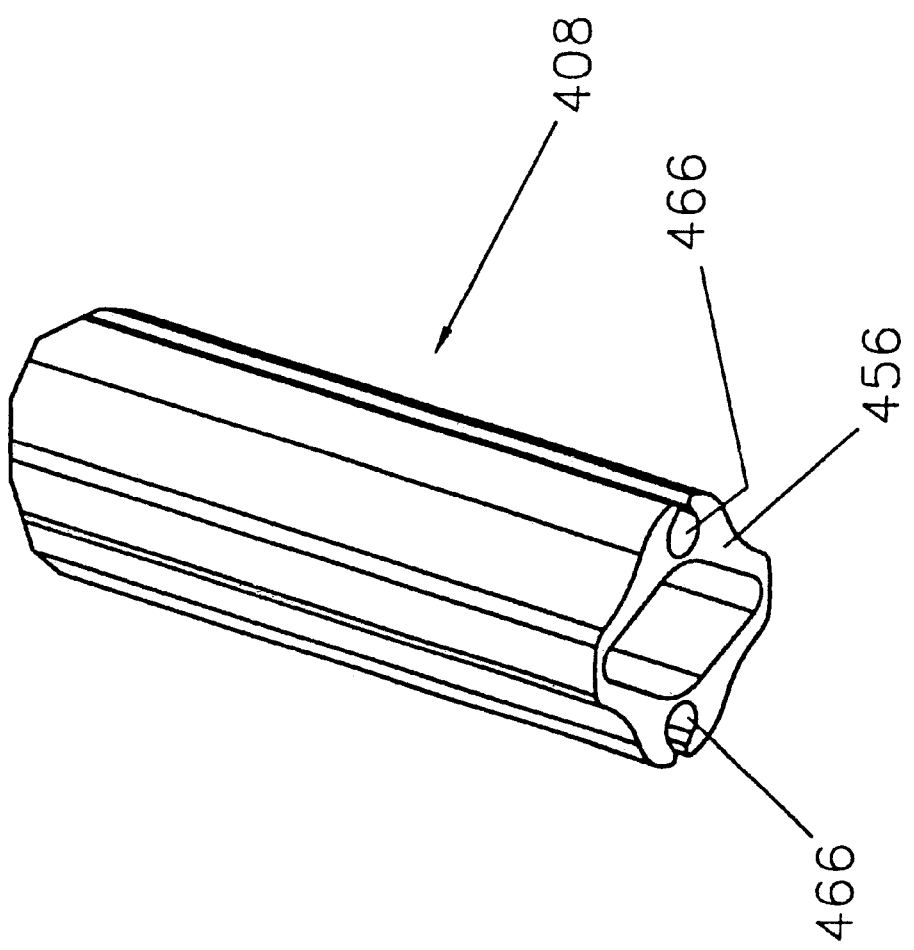
FIG. 51 is a perspective view of the distal end of the shroud component of the installation tool associated with the suture anchor assembly shown in FIG. 35.
Figure 52:
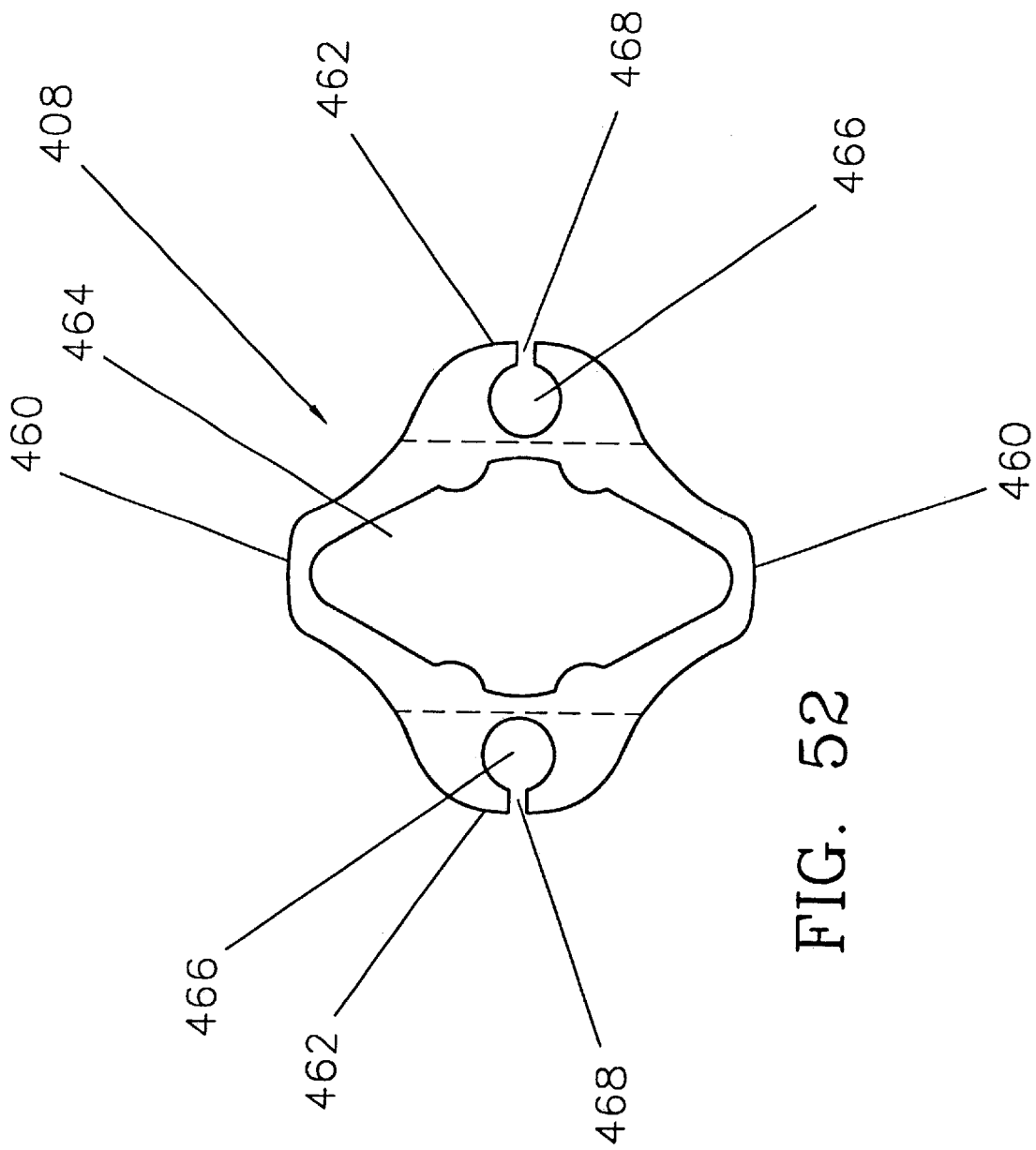
FIG. 52 is an end view of the shroud shown in FIG. 51.
Figure 53:
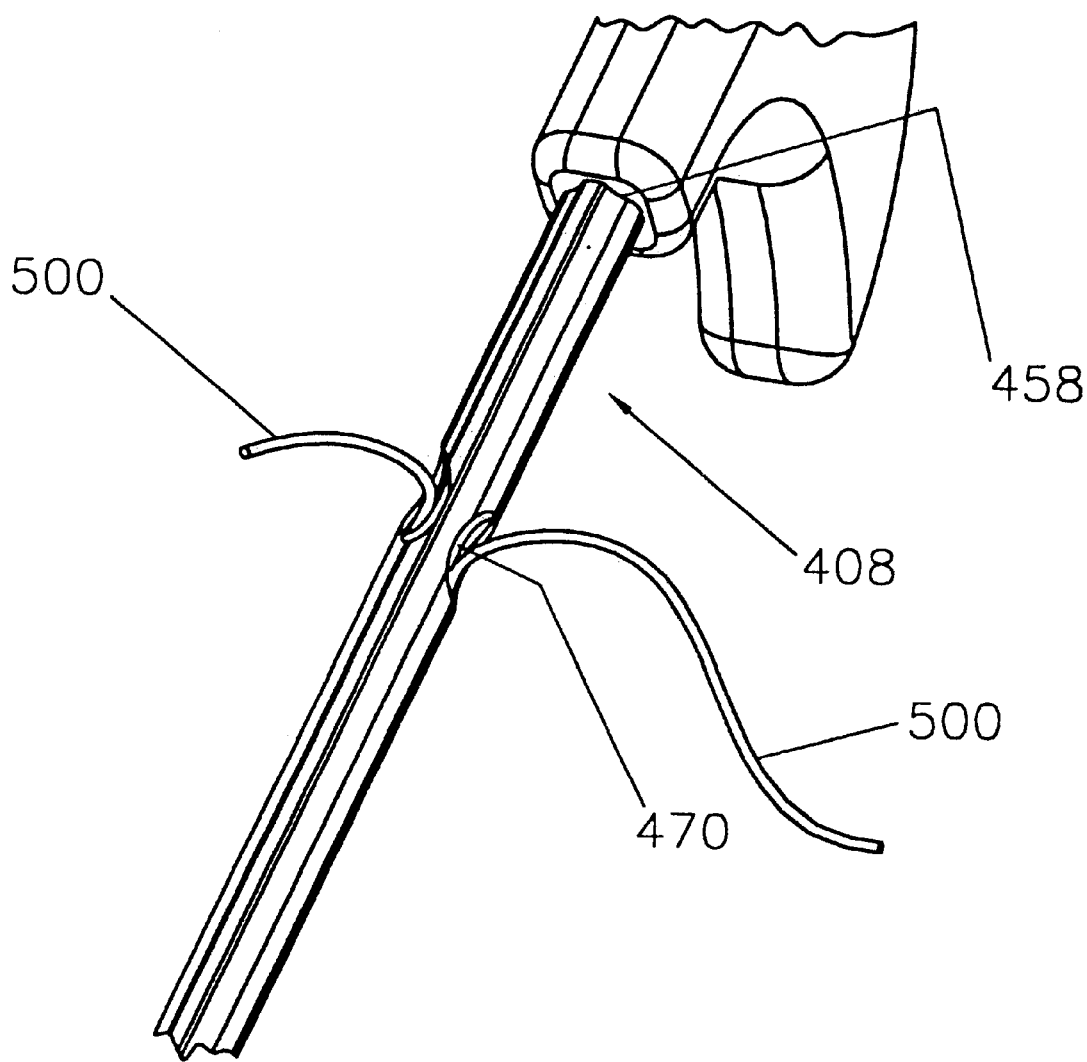
FIG. 53 is a perspective view showing the suture anchor assembly of FIG. 35 in the region where the proximal end of the shroud meets the handle member of the installation tool.
Figure 55:
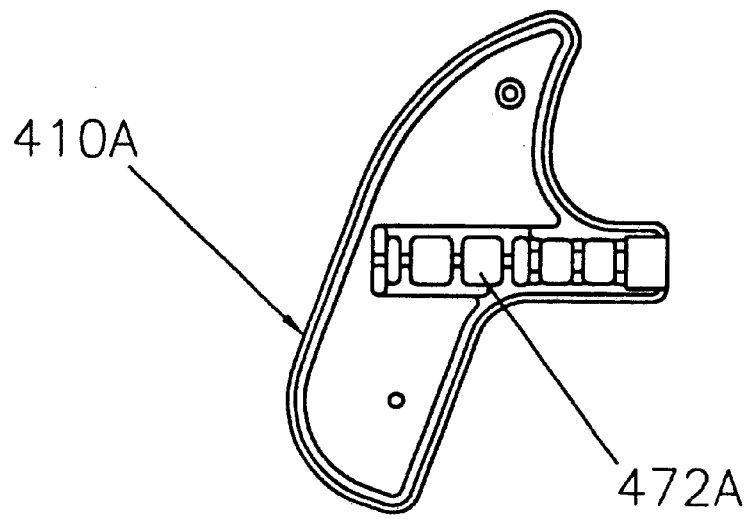
FIG. 55 is a view of the inside surface of the handle half shown in FIG. 54.
Figure 54:
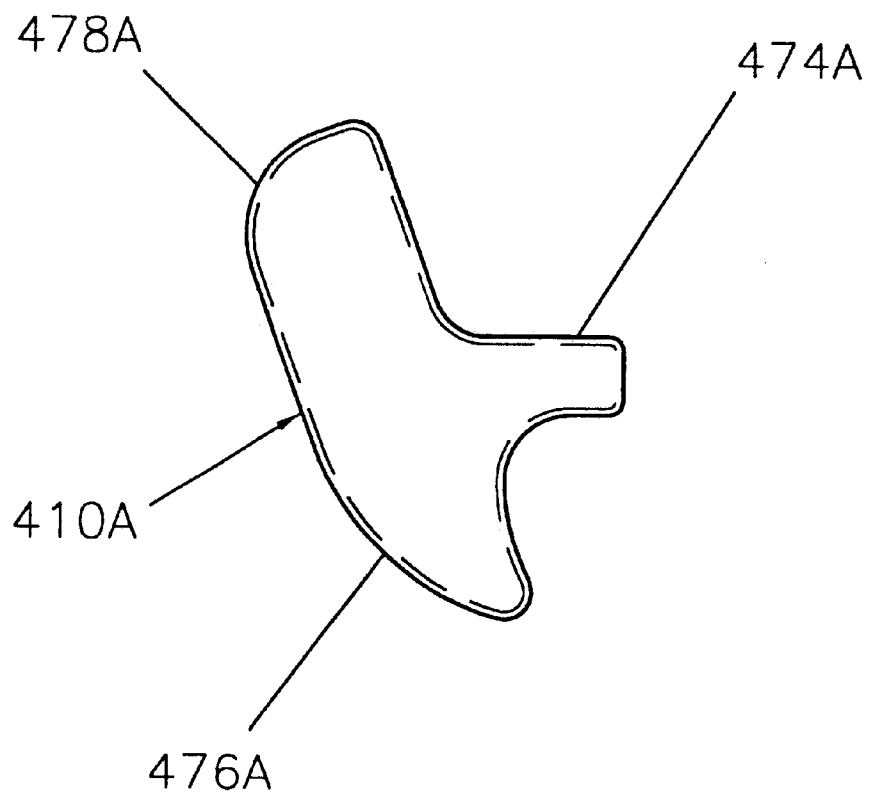
FIG. 54 is a view of the outside surface of one half of the handle of the installation tool associated with the suture anchor assembly shown in FIG. 35.
Figure 56:
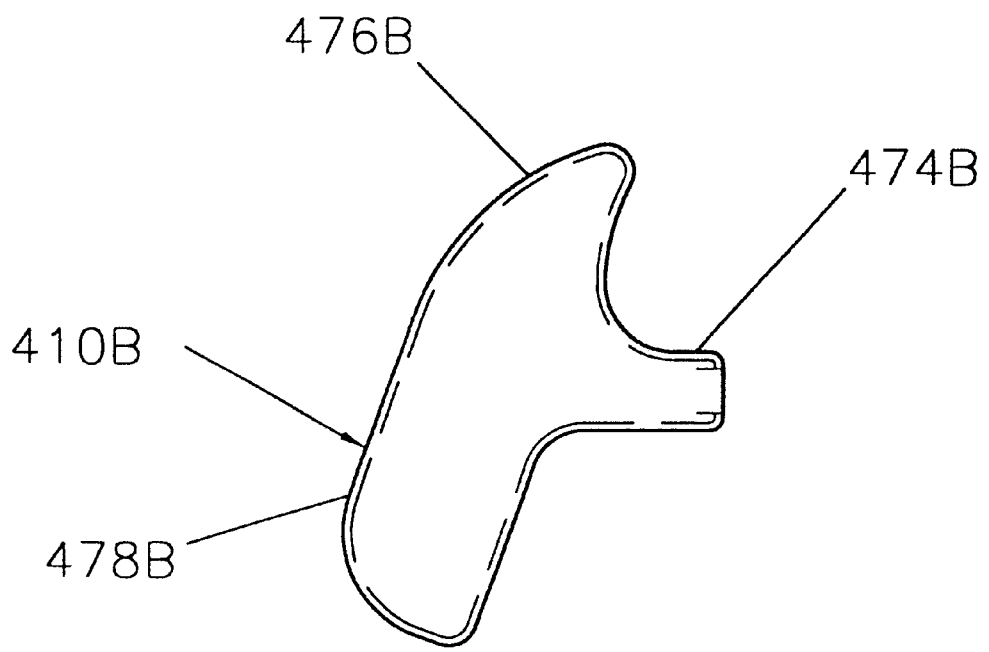
FIG. 56 is a view of the outside surface of the other half of the handle of the installation tool associated with the suture anchor assembly shown in FIG. 35.
Figure 57:
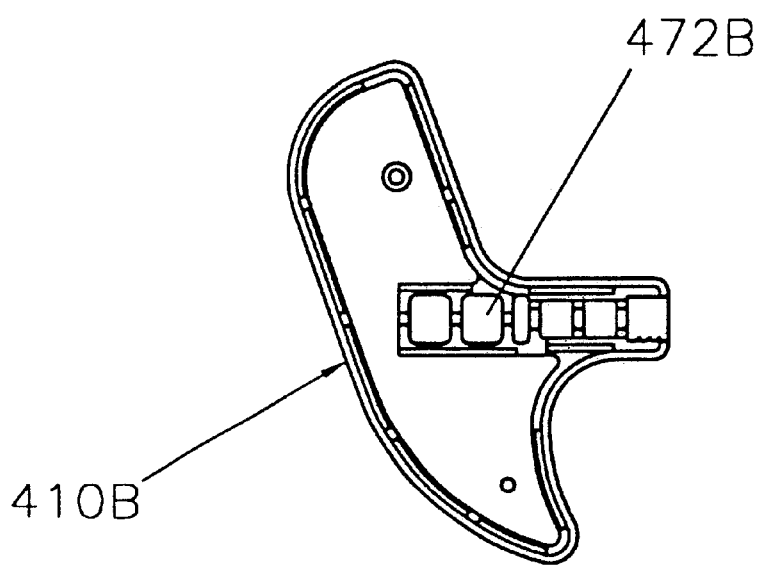
FIG. 57 is a view of the inside surface of the handle half shown in FIG. 56.

Shroud 408 is used to retain suture 500 on installation tool 400 until that suture is to be deployed at the surgical site. Shroud 408 is shown in greater detail in FIGS. 51–53. It comprises a relatively flexible body terminating in a distal end surface 456 and a proximal end surface 458. The shroud's body has a generally four-sided configuration, including a pair of diametrically-opposed sides 460, forming ridge portions, and a pair of diametrically-opposed sides 462. An elliptically-shaped internal opening 464 opens on, and extends between, distal end surface 456 and proximal end surface 458. Internal opening 464 is arranged so that its long axis is aligned with the shroud's sides 460, while its short axis is aligned with the shroud's sides 462. Internal opening 464 is sized so the installation tool's main shaft 402 can be received within internal opening 464, with main shaft 402 making a close sliding fit across the internal opening's short axis, as will hereinafter be discussed in further detail.

Each of the shroud's sides 462 includes a longitudinally-extending channel 466. Each of the channels 466 communicates with the region external to the shroud via a corresponding longitudinally-extending slot 468. Channels 466 are preferably sized so as to have a diameter approximately the same as the diameter of suture 500, while slots 468 are sized so as to have a width somewhat less than the diameter of suture 500. Each of the shroud's sides 462 is recessed or scalloped away (as at 470) for a short length near the proximal end of the shroud so as to open the full diameter of each of the channels 466 to the region external to the shroud.

Shroud 408 may be formed out of any appropriate material, e.g., it may be formed out of a soft compliant polymer such as nylon or polypropylene.

It is to be appreciated that, on account of the foregoing construction, (i) by pressing on the shroud's opposing ridge portions (i.e., sides 460), slots 468 can be made to widen so as to permit suture 500 to be laid down in channels 466, and (ii) by relaxing pressure on the shroud's opposing sides 460, slots 468 can be made to return to their normal, narrower width so as to retain suture 500 in channels 466. It is also to be appreciated that, inasmuch as shroud 408 is formed out of a relatively flexible material, any suture 500 disposed in channels 466 can be pulled free of the channels with an appropriate withdrawal force, whereby the suture can be freed from the installation tool. In particular, suture 500 can be freed from installation tool 400 by pulling the suture in an axial direction relative to the installation tool, whereby the suture will be drawn out of the ends of channels 466; or suture 500 can be freed from installation tool 400 by pulling the suture at an angle to the installation tool, whereby the suture will be peeled out of channels 466 via a deformation of slots 468.

Looking next at FIGS. 35, 43 and 54–57, handle 410 is preferably formed out of two halves 410A and 410B which are attached together so as to form the complete handle 410. Handle 410 comprises a contoured recess 472 (which is in turn formed out of contoured hemi-recesses 472A and 472B) which is configured so as to make a tight fit about the correspondingly contoured proximal end of main shaft 402, whereby handle 410 can be securely mounted to main shaft 402 and thus used to manipulate installation tool 400. The exterior configuration of handle 410 includes a first protrusion 474, a second protrusion 476 and a third protrusion 478. First protrusion 474 is aligned with the installation tool's main shaft 402 along an axis 480 (FIG. 35). Second and third protrusions 476 and 478 are aligned with one another along another axis 482. Axis 482 is set an inclined angle relative to axis 480. Preferably, axis 482 is set at an angle of about 70° (as measured along the arc 484 in FIG. 35), although angles of about 45° to about 85° are also appropriate. Thus, first, second, and third protrusions 474, 476 and 478 form an inclined "T", configuration. Second and third protrusions 476 and 478 are sized so that they will together form a natural handle for a user, e.g., so that the user's thumb and forefinger can comfortably engage second protrusion 476 while the user's remaining fingers engage third protrusion 478. As a result of the foregoing construction, the user will be able to comfortably grasp the installation tool's handle 410 and, with the pad of the hand engaging the handle's proximal surface 486, thereafter thrust the installation tool distally along the axis 480, as will hereinafter be discussed.

Suture anchor assembly 200 is intended to be assembled as follows. First, installation tool 400 is assembled, then suture anchor 300 is attached to the assembled installation tool, and finally suture 500 is attached to suture anchor 300 and installation tool 400.

Installation tool 400 is intended to be assembled as follows.

Figure 58:
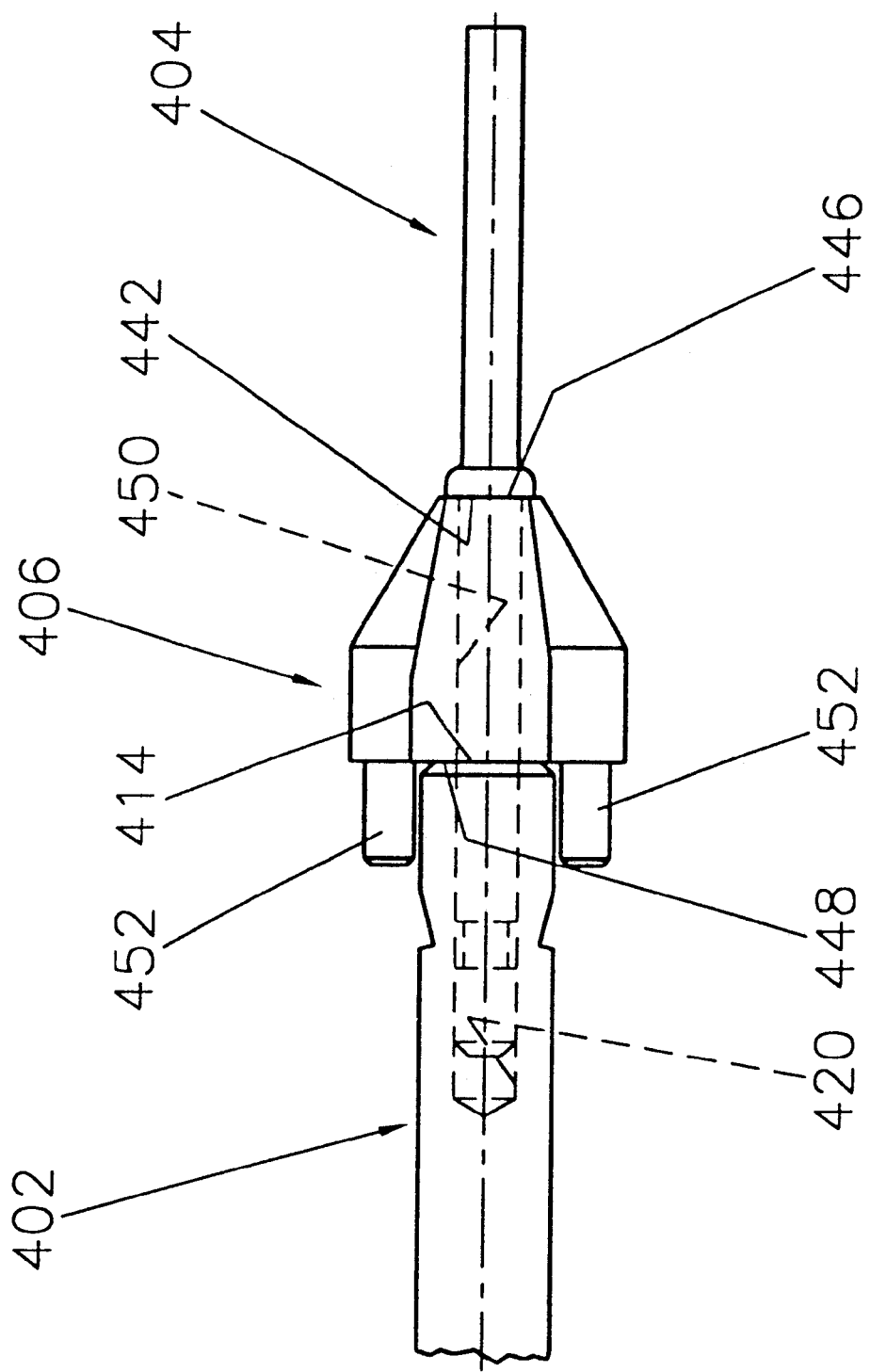
FIG. 58 is a view showing the shaft tip, nose and main shaft of the installation tool associated with the suture anchor assembly shown in FIG. 35, with the various components being assembled into a sub-assembly.

First, main shaft 402, shaft tip 404 and nose 406 are assembled into a subassembly such as shown in FIG. 58. This is done by mounting nose 406 on shaft tip 404 by inserting the proximal end of the shaft tip through axial hole 450 of the nose until the shaft tip's proximally-facing shoulder 442 engages the nose's distal end surface 446, and then mounting shaft tip 404 on main shaft 402 by inserting the proximal and of the shaft tip in the main shaft's blind hole 420 until the main shaft's distal end surface 414 engages the nose's proximal end surface 448. The proximal end of shaft tip 404 is made fast in main shaft 402 by crimping or by other means well known in the art. As a result of the foregoing construction, nose 406 is effectively captured between the shaft tip's proximally-facing shoulder 442 and the main shaft's distal end surface 414.

Next, shroud 408 is loaded onto the aforementioned subassembly. This is done by first aligning main shaft 402 with the shroud's internal opening 464, with the two posts 452 of the nose being aligned with the long axis of the elliptically-shaped opening 464. Then the proximal end of main shaft 402 is passed through the shroud's internal opening 464 until the two posts 452 of the nose enter the shroud's internal opening 464 and the shroud's distal end surface 456 seats firmly against the nose's proximal end surface 448. At this point each of the two surface grooves 454 of nose 406 will be aligned with one of the channels 466 of shroud 408, with main shaft 402 making a close sliding fit across the short axis of the shroud's internal axis 464.

Next, handle 410 is attached to the proximal end of main shaft 402. This is done by fitting the proximal end of main shaft 402 in either hemi-recess 472A of handle half 410A or hemi-recess 472B of handle half 410B, and then placing the corresponding complementary second handle half (i.e., either handle half 410B or handle half 410A, respectively) in place, and finally making the two handle halves fast to one another in ways well known in the art (e.g., by ultrasonic welding), whereby they will be securely attached to the proximal end of main shaft 402. It is to be appreciated that when handle 410 is so mounted to main shaft 402, the distal end of the handle's first protrusion 474 will substantially engage the shroud's proximal end surface 458. It is also to be appreciated that handle 410 is mounted to main shaft 402 such that the plane extending between the two handle halves 410A and 410B will be aligned with the major axis of the shroud's internal opening 464, with one of the shroud's channels 466 being aligned with each handle half, and with the one of the shroud's recessed or scalloped sections 470 being aligned with, and residing adjacent to, each handle half.

It is to be appreciated that inasmuch as main shaft 402 and shaft tip 404 are formed out of two separate elements which are securely attached together, each element can be designed for its own particular requirements. In particular, main shaft 402 can be designed so as to provide the desired rigidity, whereas shaft tip 404 can be designed so as to provide the desired flexibility; yet the two elements are securely attached to one another so as to together operate as the desired unit.

Suture anchor 300 is attached to the assembled installation tool 400 as follows. First, suture anchor 300 and installation tool 400 are oriented so that the distal end of shaft tip 404 is aligned with the suture anchor's blind hole 334. Then suture anchor 300 and installation tool 400 are brought together as they are simultaneously turned relative to one another, whereby the suture anchor will be mounted on the distal end of the installation tool's shaft tip 404, with the threaded portion 428 of shaft tip 404 being threadedly mounted in the suture anchor's bore 338, and with the immediately-proximal portion 432 of the shaft tip being received in the suture anchor's counterbore 340. It is to be appreciated that due to the relative sizing of the suture anchor's blind hole 334 (see FIG. 59) and the shaft tip's distal end 424, the shaft tip's threaded portion 428 will make a threaded engagement with the suture anchor within bore 338, but the shaft tip's immediately-proximal portion 432 will not be secured to the suture anchor within counterbore 340.

Figure 60:
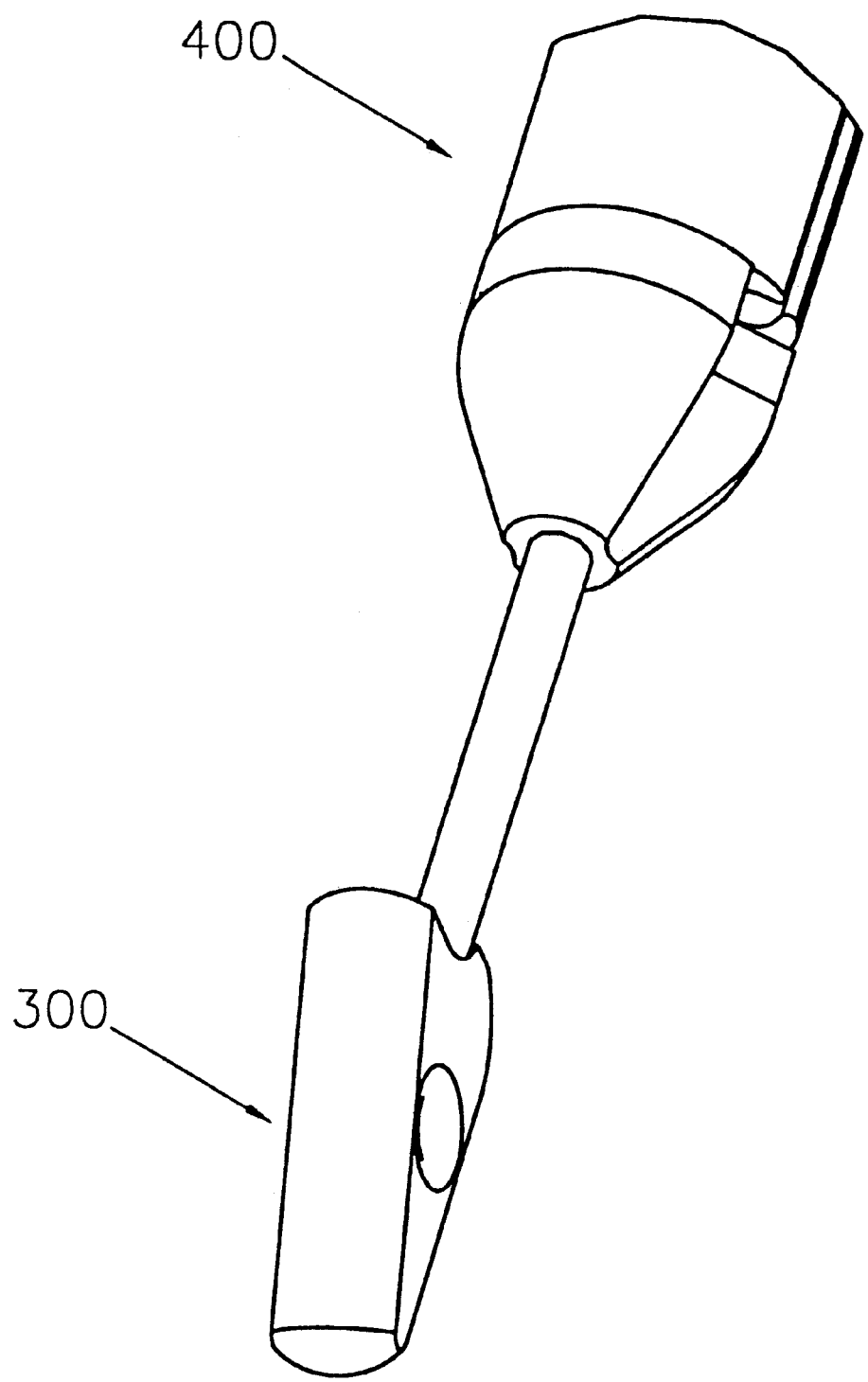
FIG. 60 is a perspective view of the distal end of the suture anchor assembly shown in FIG. 35, with the assembly's suture element removed.

Suture anchor 300 and installation tool 400 are arranged so as to have a specific orientation relative to one another, i.e., so that the suture anchor's two side surfaces 320 extend parallel to the plane extending between the two handle halves 410A and 410B, with the suture anchor's abutment surface 312 being aligned with the handle's second protrusion 476 and the suture anchor's plow surface 316 being aligned with the handle's third protrusion 478 (see FIGS. 35, 36 and 60). It is to be appreciated that, on account of the foregoing arrangement, the user will always know the orientation of suture anchor 300 simply by knowing the orientation of the installation tool's handle 410. This can be an important feature in certain types of surgery where the suture anchor may have to be set with a particular orientation and the user's view of the suture anchor itself may be restricted.

Figure 61:
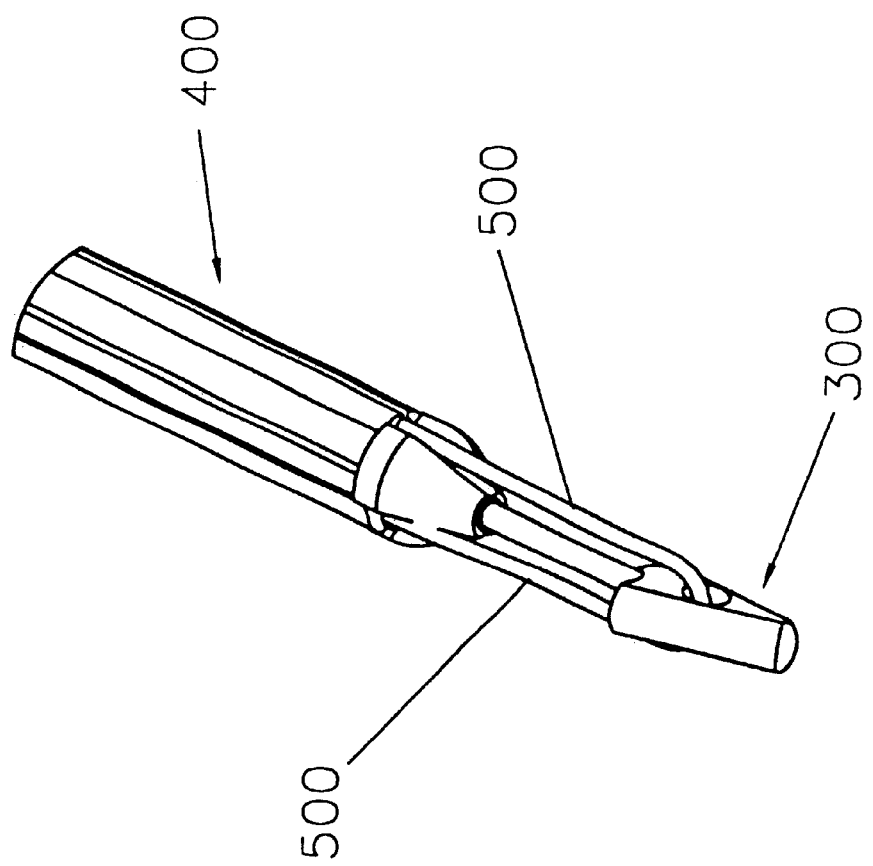
FIG. 61 is a perspective view showing the distal end of the suture anchor assembly shown in FIG. 35, with the assembly's suture element in place.

Next, suture 500 is attached to suture anchor 300 and installation tool 400. This is done by passing suture 500 through the suture anchor's through-hole 330 and then positioning the suture within the shroud's longitudinally-extending channels 466. In this respect it will be appreciated that suture 500 can be easily positioned in channels 466 by first pressing on the shroud's opposing side surfaces 460 so as to open slots 468, then laying down suture 500 within the opened channels 466, and then releasing the shroud's opposing side surfaces 460 so as to releasably capture the suture within channels 466. The proximal ends of suture 500 are arranged so that they exit the shroud adjacent to recessed or scalloped portions 470, where they rest free adjacent to handle 410 (see FIGS. 36, 53 and 61).

Suture anchor assembly 200 is intended to be used as follows.

Figure 62:
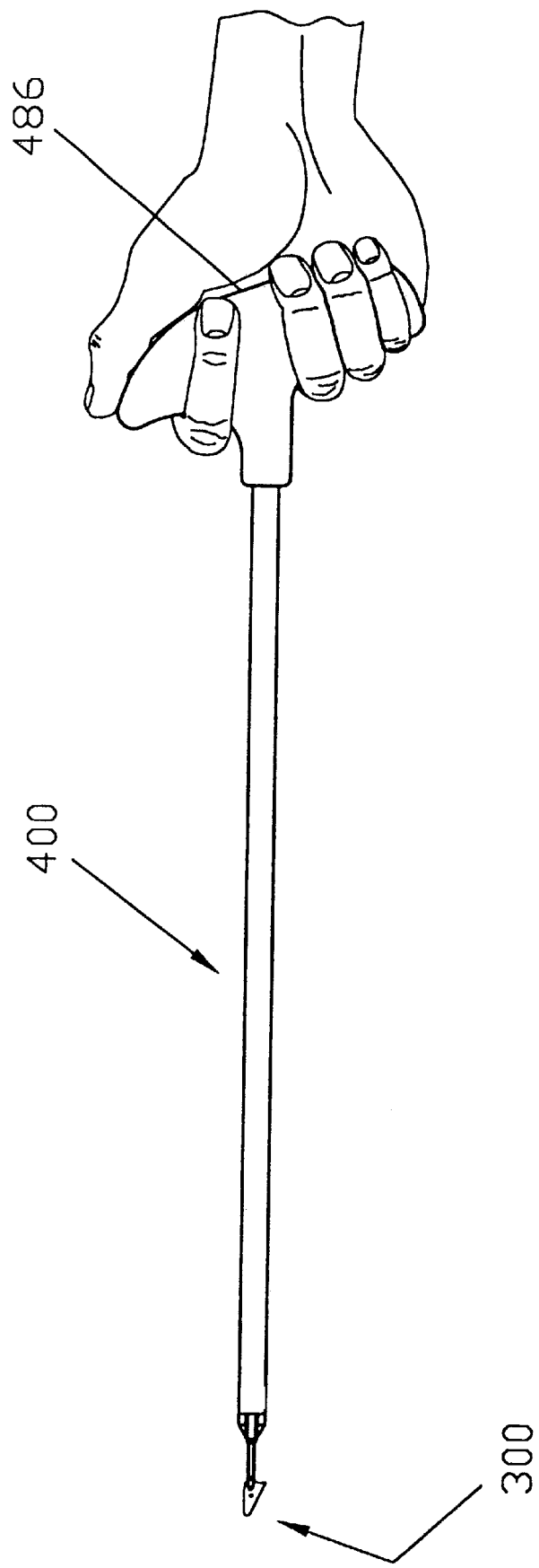
FIG. 62 is a view showing the suture anchor assembly of FIG. 35 being gripped by the hand of a user.

First, suture anchor assembly 200 is picked up by the user so that the user's thumb and forefinger engage the handle's second protrusion 476 and the user's remaining fingers engage the handle's third protrusion 478, and so that the handle's proximal surface 486 sits against the heel of the user's hand (see FIG. 62). It is to be appreciated that when the suture anchor assembly is held in this manner, the apparatus will be ready to drivingly insert the suture anchor in a bore hole formed in a bone. Furthermore, in view of the fact that the suture anchor is mounted to the installation tool with a predetermined orientation, the user will always know the relative positioning of the suture anchor's abutment surface 312, its plow surface 316, and its sharp, well-defined biting edge 322, even if the suture anchor itself is not directly visible to the user.

Next, the user uses installation tool 400 to drive suture anchor 300 into a bore hole. This is done by aligning suture anchor 300 with a bore hole 600 formed in a bone 601 (FIG. 63) and then pushing the suture anchor into the bone hole. As this occurs, the suture anchor's plow surface 316 will first tend to engage rim 603 of bore hole 600, causing the distal end of shaft tip 404 to flex as the suture anchor pivots to enter the bore hole. Further downward pressure on the installation tool's handle 410 causes the distal end of the shaft tip to flex even further as the suture anchor's plow surface 316 engages, and then rides along, wall 602 of the bore hole, with the suture anchor's cam surface 326 being slightly spaced from, or insignificantly in contact with, the bore hole's opposing wall 606 (see FIG. 64). Significantly, such flexing of the distal end of shaft tip 404 does not significantly undermine the attachment of suture anchor 300 to installation tool 400, since only the distalmost portion of the shaft tip (i.e., the threaded portion 428) is actually secured to the suture anchor, with the shaft tip's immediatelyproximal portion 432 being free to flex slightly within the suture anchors counterbore 340 without damaging the suture anchor. This is true even where suture anchor 300 may be formed out of a non-metallic material, e.g., a plastic or absorbable material.

The user pushes suture anchor 300 downward into bore hole 600 until the desired depth is reached. Such downward pressure keeps the suture anchor's plow surface 316 in engagement with the bore hole's wall 602. Preferably installation tool 400 is sized so that nose 406 engages the top surface 604 of bone 601 when the desired depth is reached.

Next, the user withdraws installation tool 400 from bore hole 600. As downward pressure on installation tool 400 is released (to be replaced by opposite upward pressure during tool withdrawal), the flexed shaft tip 404 tries to straighten itself, causing the suture anchors sharp, well-defined biting edge 322 to press into wall 602, and causing the suture anchor to pivot slightly in the bore hole so that the suture anchor's cam surface 326 securely engages wall 606 of the bore hole. As the user retracts installation tool 400 from bore hole 600, rearward movement of installation tool 400 causes progressively more distal portions of the suture anchor's cam surface 326 to come into engagement with wall 606 of the bore hole. Since cam surface 326 is arranged to cam the suture anchor laterally, such engagement of cam surface 326 with bone wall 606 causes the anchor's sharp, well-defined biting edge 322 to be driven progressively further and further into wall 602 of the bore hole, until the suture anchor's abutment surface 312 rests against wall 606 (FIG. 65). As installation tool 400 is pulled further back, the installation tool eventually breaks free from the lodged suture anchor. The installation tool is then withdrawn from the surgical site.

It should be appreciated that the presence of cam surface 326 significantly enhances the ability of suture anchor 300 to set in bone 601, since the cam surface provides a force on the suture anchor's edge surface 322 which is approximately normal to the bore hole's wall 602. This force drives the suture anchor's edge surface 322 into wall 602, ensuring that the suture anchor will be reliably set. This is true even where bone 601 is relatively hard (e.g., cortical bone) and the suture anchor is made out of a non-metallic material, e.g., plastic or a bioabsorbable material.

By changing the geometry of cam surface 326, the setting characteristics of suture anchor 300 can be adjusted.

It should also be appreciated that the nature of the attachment of suture anchor 300 to installation tool 400 is important. In particular, the suture anchor must be attached to the installation tool securely enough to cause the suture anchor to turn in the aforementioned camming action, yet release at the appropriate time so as to leave the suture anchor in the bone as the installation tool is withdrawn. Thus it is desirable that the connection between suture anchor 300 and installation tool 400 be well defined at the time of manufacture, and remain intact up until the time that the installation tool breaks free from the anchor. In particular, it is important that this connection not be undermined while the distal end of the installation tool flexes in the bore hole. It has been found that such a reliable connection can be established by providing the distal end of the shaft tip with a threaded portion 428 and an immediately-proximal smooth portion 432, and providing suture anchor 300 with a bore 338 and a counterbore 340, where the shaft tip's threaded portion 428 makes a threaded engagement with the suture anchor within bore 338, but the shaft tip's immediately-proximal portion 432 is not secured to the suture anchor within counterbore 340. This permits the necessary flexing of the shaft tip to occur without undermining the connection between the installation tool and the suture anchor, even where the suture anchor is formed out of a non-metallic material, e.g., a plastic or absorbable material.

It is to be appreciated that as installation tool 400 separates from the deployed anchor 300, suture 500 can simultaneously slide along the inner surfaces of the shroud's channels 466, so as to permit the two members to separate. Depending on the length of suture 500 and the degree of separation imposed, suture 500 may or may not be fully removed from installation tool 400 during anchor deployment. To the extent that some of suture 500 remains attached to installation tool 400 after the installation tool has been withdrawn, the installation tool may be placed on a surgical drape adjacent to the surgical site until the suture 500 is to be completely removed from the installation tool. At that point the remaining suture may be pulled free of the installation tool.

For many procedures, retaining a portion of suture 500 in installation tool 400 until needed can be helpful for effective suture management. For example, where an arthroscopic procedure involves more than one suture anchor, the paired suture ends of several suture anchors might emanate from a single cannula opening. By way of example, an arthroscopic Bankhart procedure could involve four or even six suture lengths emanating from a single cannula opening. In such a situation, retaining suture lengths in the installation tool can help keep the suture lengths more easily identifiable for the surgeon.

Additionally, and/or alternatively, to help improve suture management, it may be desired to mark various suture lengths. For example, each suture length could be distinctively color-coded, or distinctively pattern-coded. U.S. Pat. No. 3,949,755 issued Apr. 13, 1976 to Vauquois teaches the provision of contrasting shades on suture, which patent is hereby incorporated herein by reference.

It is also possible to modify the suture anchor 300 described above.

For example, in the suture anchor 300 described above, the suture anchor's through-hole 330 is preferably sized so as to slidably receive a single strand of suture. However, if desired, the suture anchor's through-hole 330 could be sized so as to slidably receive multiple stands of suture simultaneously. Of course, if such a construction were used, the shroud's channels 466 should be correspondingly enlarged so as to accommodate the additional suture lengths provided, or some other provision should be made to manage the additional suture ends present with such a construction.

Figure 66:
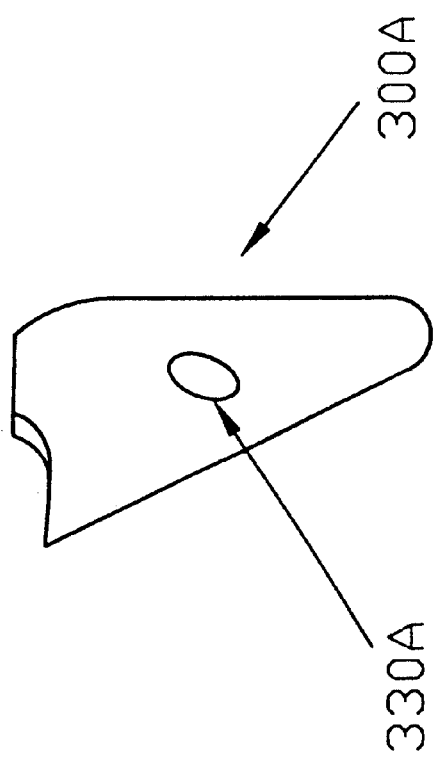
FIG. 66 is a side view showing an alternative form of suture anchor.

Furthermore, with the suture anchor 300 described above, the suture anchor's through-hole 330 is formed so as to have a substantially round configuration. However, the suture anchor's through-hole can also be formed with an elliptical configuration, such as the through-hole 330A provided in the suture anchor 300A shown in FIGS. 66–68. By forming the suture anchor's through-hole with an elliptical configuration, stresses from the suture can be directed to specific portions of the suture anchor. In particular, these suture stresses can be directed to more robust portions of the suture anchor, thereby enabling the suture anchor to carry larger loads. This feature can be particularly useful where the suture anchor is formed out of a non-metallic material, e.g. a plastic or bioabsorbable material. In addition, by forming the suture anchor's through-hole with an elliptical configuration, subsequent proximal pulling of the suture can also help to further set the suture anchor with a desired orientation within the bone.

Figure 70:
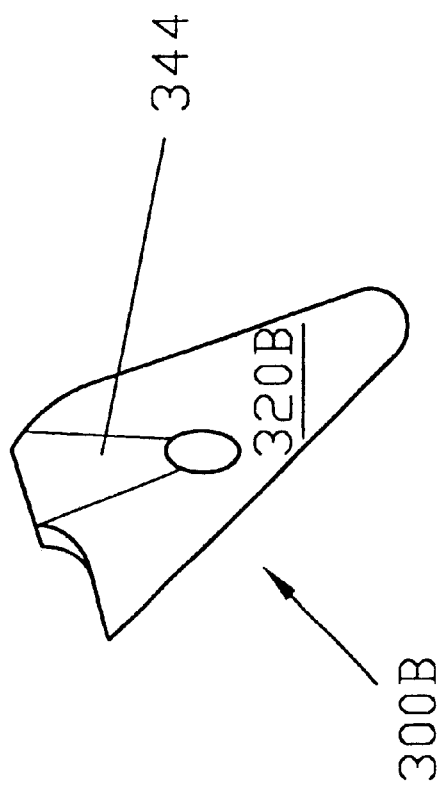
FIG. 70 is a view of a side of an alternative form of suture anchor formed in accordance with the present invention.
Figure 71:
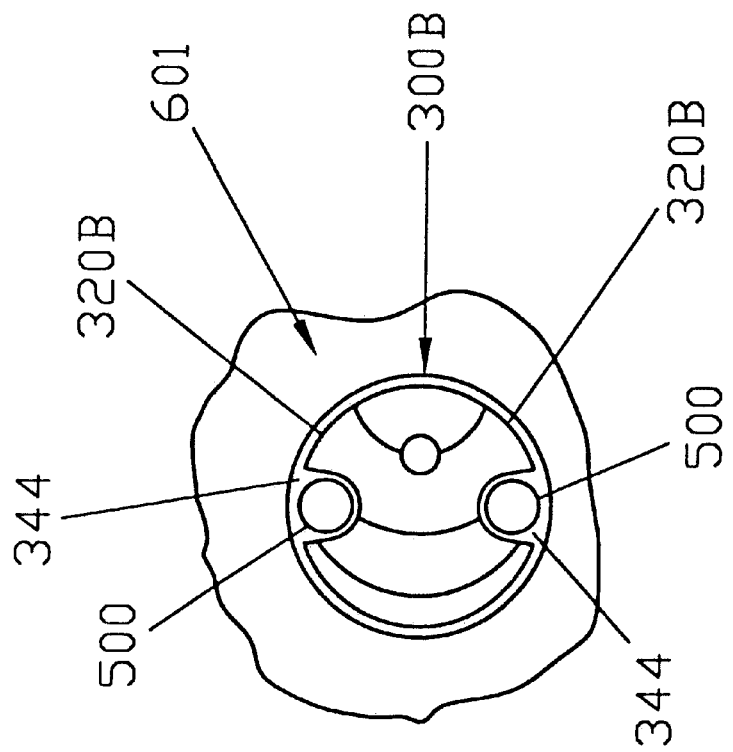
FIG. 71 is a proximal end view of the suture anchor of FIG. 70 disposed in a bore hole.
Figure 69:
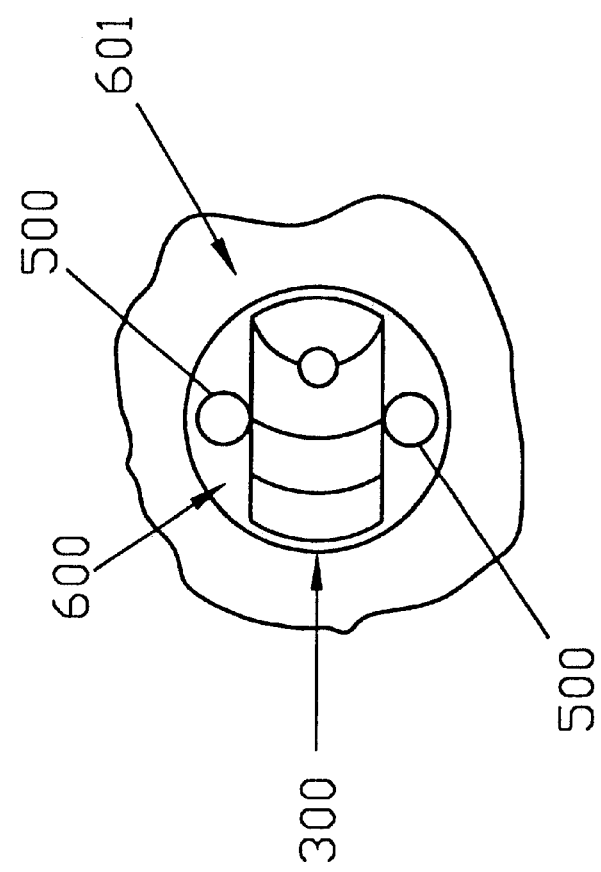
FIG. 69 is a top end view showing the suture anchor of FIG. 66 disposed in a bore hole.

Also, with the suture anchor 300 described above, the suture anchor is configured so as to have substantially planar side surfaces 320. As a result, the anchor must be formed thin enough so that the suture lengths emanating from the anchor can pass alongside the suture anchor within the bore hole (see FIG. 69). This is particularly true where it is desired to slide suture 500 relative to suture anchor 300 when the suture anchor is set in a bone hole. However, in many situations it can be advantageous to form the suture anchor with the thickest possible configuration, with the sides of the suture anchor having a rounded outer surface, e.g., such as the side surfaces 320B provided for the suture anchor 300B shown in FIGS. 70 and 71. In this situation, a pathway 344 must be provided to permit suture 500 to pass from the suture anchor's through-hole 330 to the exterior of the bone. In this respect it should also be appreciated that inasmuch as the suture anchor must rotate within the bone, the pathways 344 should be formed with a configuration which broadens toward the proximal end of the anchor, in the manner schematically illustrated in FIG. 70. Such a construction permits the necessary anchor rotation to occur without causing the suture to come into abrasive engagement with the side walls of the bore hole.

Figure 73:
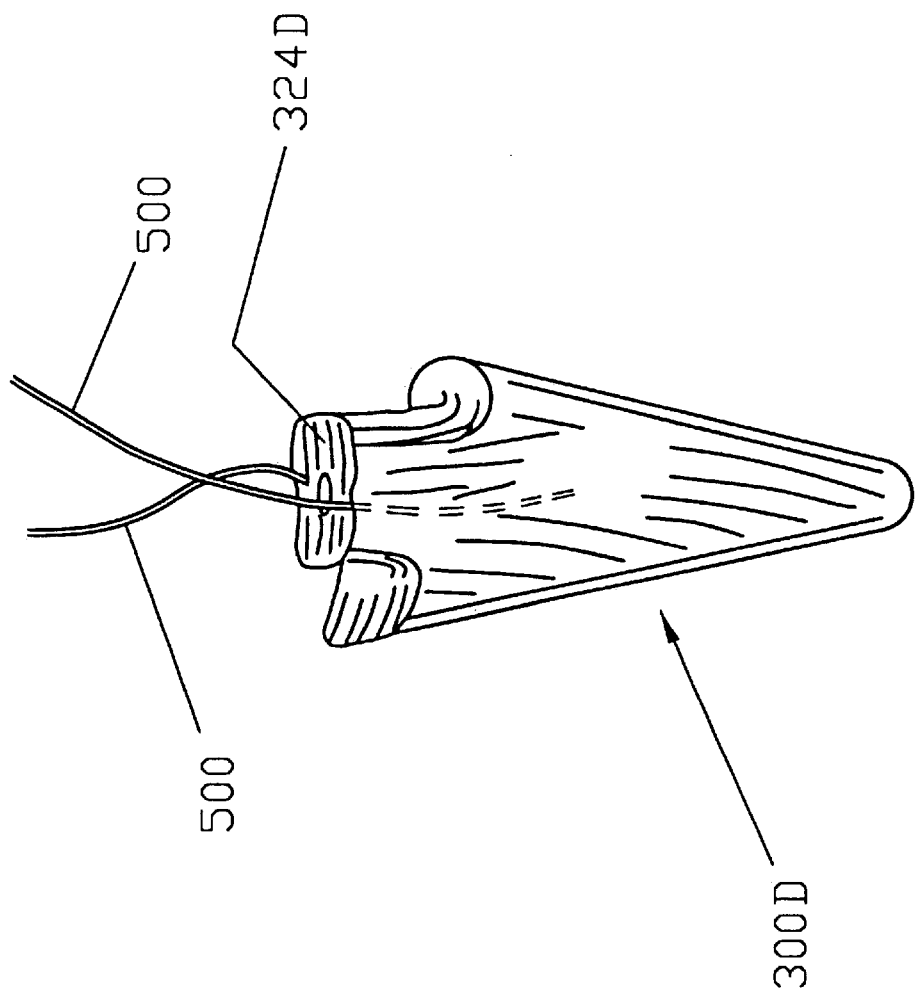
FIG. 73 is a perspective view showing another form of suture anchor formed in accordance with the present invention.

Also, it is possible to omit the suture anchor's through-hole 330 and attach the suture directly to the anchor. Thus, for example, a suture anchor 300C is shown in FIG. 72 where the suture 500 is molded or fused directly into the side 320C of the body of the anchor. Alternatively, and looking now at FIG. 73, the suture 500 could enter the proximal end surface 324D of a suture anchor 300D and then be internally fused to the interior of the suture anchor. This could be done with a single suture strand, or with a pair of independent suture strands, or with a looped suture strand where the loop is fused within the interior of the body.

It is also possible to attach a suture to the suture anchor by forming a longitudinal hole through the suture anchor, passing the suture through that longitudinal hole, and then knotting the suture at the distal end of the suture anchor so as to prevent the suture from being withdrawn proximally through the suture anchor.

Figure 74:
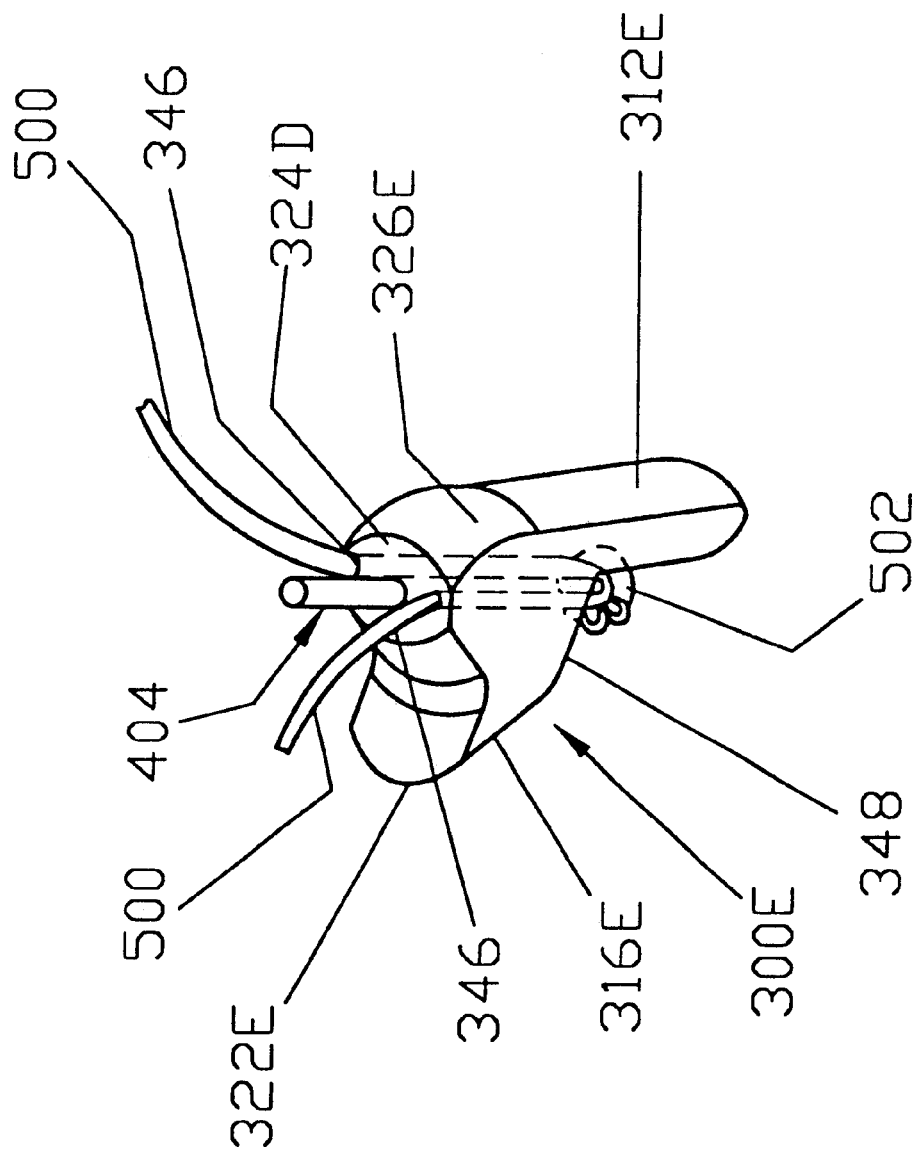
FIG. 74 is a perspective view showing another form of suture anchor formed in accordance with the present invention.

Alternatively, an enlargement of some other sort could be positioned at the distal end of the suture to prevent suture withdrawal. Thus, for example, a suture anchor 300E is shown in FIG. 74, wherein suture 500 passes through a pair of longitudinal holes 346 opening on proximal end surface 324D, and then are knotted at a knot 502 near the distal end of the anchor. If desired, a recess or cutaway 348 can be provided near the distal end of the anchor to accommodate knot 502. Alternatively, a single suture strand 500 could be used, with the suture strand passing down one longitudinal hole 346 and back up the other longitudinal hole, whereby the use of the knot 502 could be eliminated.

Thus, the invention has been described with reference to the attached drawings. It is easily understood by one of ordinary skill in the art that changes may be made to the embodiments described herein without exceeding the spirit or scope of the attached claims.

What is claimed is:

1. A suture anchor for disposition in a bore in a bone, the anchor comprising:

a substantially wedge-shaped body having a smaller distal end and larger proximal end, means thereon for retaining a suture, and means thereon for releasable connection to an inserter shaft;

said body distal end being of rounded configuration;

a plow surface of said body being of rounded configuration in plan view;

an abutment surface of said body opposite from said plow surface being of rounded configuration in plan view; and said abutment surface and a boundary surface of said body intersecting to form, in side elevational view, a rounded configuration;

said rounded configurations being operable to guide entry of said body into the bore in the bone and to center said body in the bore.

\* \* \* \* \*